United States Patent
Shelton, IV et al.

(10) Patent No.: US 8,357,085 B2
(45) Date of Patent: Jan. 22, 2013

(54) DEVICES AND METHODS FOR PROVIDING ACCESS INTO A BODY CAVITY

(75) Inventors: Frederick E. Shelton, IV, Hillsboro, OH (US); Carl J. Shurtleff, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 371 days.

(21) Appl. No.: 12/479,418

(22) Filed: Jun. 5, 2009

(65) Prior Publication Data

US 2010/0249525 A1   Sep. 30, 2010

Related U.S. Application Data

(60) Provisional application No. 61/165,080, filed on Mar. 31, 2009.

(51) Int. Cl.
*A61B 17/34* (2006.01)
(52) U.S. Cl. .......................................... 600/208; 600/203
(58) Field of Classification Search .................. 600/203, 600/206, 208, 215; 604/167.01, 167.03, 604/167.07
See application file for complete search history.

(56) References Cited

U.S. PATENT DOCUMENTS

| | | |
|---|---|---|
| 2,129,391 A | 9/1938 | Wappler |
| 3,402,710 A | 9/1968 | Paleschuck |
| 3,503,396 A | 3/1970 | Pierie et al. |
| 3,654,965 A | 4/1972 | Gramain |
| 4,041,931 A | 8/1977 | Elliott et al. |
| 4,048,987 A | 9/1977 | Hurson |
| 4,112,932 A | 9/1978 | Chiulli |
| 4,120,302 A | 10/1978 | Ziegler |
| 4,306,545 A | 12/1981 | Ivan et al. |
| 4,373,532 A | 2/1983 | Hill et al. |
| 4,379,458 A | 4/1983 | Bauer et al. |
| 4,402,683 A | 9/1983 | Kopman |
| 4,417,888 A | 11/1983 | Cosentino et al. |
| 4,559,947 A | 12/1985 | Renger et al. |
| 4,669,473 A | 6/1987 | Richards et al. |
| 4,821,719 A | 4/1989 | Fogarty |
| 4,831,070 A | 5/1989 | McInally et al. |
| 5,010,925 A | 4/1991 | Atkinson et al. |
| 5,027,800 A | 7/1991 | Rowland |
| 5,091,435 A | 2/1992 | Suzuki et al. |
| 5,121,298 A | 6/1992 | Sarma et al. |

(Continued)

FOREIGN PATENT DOCUMENTS

CA   2095064 A1   11/1993

(Continued)

OTHER PUBLICATIONS

International Search Report and Written Opinion for International App. No. PCT/US2010/036811 dated Sep. 14, 2010 (6 pages).

(Continued)

*Primary Examiner* — Ralph Lewis

(57) ABSTRACT

Methods and devices are provided for accessing a body cavity. In general, a surgical access device is provided that can include a retractor that forms a working channel through tissue, a seal housing for sealing the working channel and/or forming a seal around an instrument inserted therethrough, and a flexible suspension member that is configured to suspend the seal housing within the body cavity or allow the seal housing to extend beyond the distal end of the retractor.

21 Claims, 10 Drawing Sheets

U.S. PATENT DOCUMENTS

| | | |
|---|---|---|
| 5,183,471 A | 2/1993 | Wilk |
| 5,197,955 A | 3/1993 | Stephens et al. |
| 5,207,213 A | 5/1993 | Auhll et al. |
| 5,209,737 A | 5/1993 | Ritchart et al. |
| 5,209,741 A | 5/1993 | Spaeth |
| 5,235,966 A | 8/1993 | Jamner |
| 5,269,772 A | 12/1993 | Wilk |
| 5,308,336 A | 5/1994 | Hart et al. |
| 5,312,417 A | 5/1994 | Wilk |
| 5,320,611 A | 6/1994 | Bonutti et al. |
| 5,330,437 A | 7/1994 | Durman |
| 5,342,315 A | 8/1994 | Rowe et al. |
| 5,345,927 A | 9/1994 | Bonutti |
| 5,362,294 A | 11/1994 | Seitzinger |
| 5,366,478 A | 11/1994 | Brinkerhoff et al. |
| 5,368,597 A | 11/1994 | Pagedas |
| 5,385,553 A | 1/1995 | Hart et al. |
| 5,385,560 A | 1/1995 | Wulf |
| 5,391,154 A | 2/1995 | Young |
| 5,398,617 A | 3/1995 | Deandrea |
| 5,431,676 A | 7/1995 | Dubrul et al. |
| 5,443,452 A | 8/1995 | Hart et al. |
| 5,443,484 A | 8/1995 | Kirsch et al. |
| 5,476,475 A | 12/1995 | Gadberry |
| 5,480,410 A | 1/1996 | Cuschieri et al. |
| 5,520,609 A | 5/1996 | Moll et al. |
| 5,531,758 A | 7/1996 | Uschold et al. |
| 5,545,123 A | 8/1996 | Ortiz et al. |
| 5,545,179 A | 8/1996 | Williamson, IV |
| 5,547,458 A | 8/1996 | Ortiz et al. |
| 5,562,677 A | 10/1996 | Hildwein et al. |
| 5,569,205 A | 10/1996 | Hart et al. |
| 5,569,254 A | 10/1996 | Carlson et al. |
| 5,582,577 A | 12/1996 | Lund et al. |
| 5,584,850 A | 12/1996 | Hart et al. |
| 5,586,977 A | 12/1996 | Dorsey, III |
| 5,591,182 A | 1/1997 | Johnson |
| 5,595,193 A | 1/1997 | Walus et al. |
| 5,624,381 A | 4/1997 | Kieturakis |
| 5,628,732 A | 5/1997 | Antoon, Jr. et al. |
| 5,630,831 A | 5/1997 | Lahr |
| 5,634,882 A | 6/1997 | Gagner |
| 5,634,883 A | 6/1997 | Chin et al. |
| 5,634,911 A | 6/1997 | Hermann et al. |
| 5,634,937 A | 6/1997 | Mollenauer et al. |
| 5,636,645 A | 6/1997 | Ou |
| 5,640,977 A | 6/1997 | Leahy et al. |
| 5,643,283 A | 7/1997 | Younker |
| 5,643,301 A | 7/1997 | Mollenauer |
| 5,647,372 A | 7/1997 | Tovey et al. |
| 5,653,705 A | 8/1997 | de la Torre et al. |
| 5,653,718 A | 8/1997 | Yoon |
| 5,665,093 A | 9/1997 | Atkins et al. |
| 5,672,168 A | 9/1997 | de la Torre et al. |
| 5,676,657 A | 10/1997 | Yoon |
| 5,681,324 A | 10/1997 | Kammerer et al. |
| 5,695,448 A | 12/1997 | Kimura et al. |
| 5,707,359 A | 1/1998 | Bufalini |
| 5,716,327 A | 2/1998 | Warner et al. |
| 5,716,407 A | 2/1998 | Knapp et al. |
| 5,728,121 A | 3/1998 | Bimbo et al. |
| 5,735,289 A | 4/1998 | Pfeffer et al. |
| 5,741,298 A | 4/1998 | MacLeod |
| 5,743,851 A | 4/1998 | Moll et al. |
| 5,752,970 A | 5/1998 | Yoon |
| 5,772,654 A | 6/1998 | Leyva |
| 5,782,812 A | 7/1998 | Hart et al. |
| 5,793,113 A | 8/1998 | Oda |
| 5,797,888 A | 8/1998 | Yoon |
| 5,803,919 A | 9/1998 | Hart et al. |
| 5,813,409 A | 9/1998 | Leahy et al. |
| 5,814,058 A | 9/1998 | Carlson et al. |
| 5,816,257 A | 10/1998 | Chin |
| 5,827,319 A | 10/1998 | Carlson et al. |
| 5,840,078 A | 11/1998 | Yerys |
| 5,843,040 A | 12/1998 | Exline |
| 5,853,395 A | 12/1998 | Crook et al. |
| 5,865,807 A | 2/1999 | Blake, III |
| 5,868,762 A | 2/1999 | Cragg et al. |
| 5,876,447 A | 3/1999 | Arnett |
| 5,882,344 A | 3/1999 | Stouder, Jr. |
| 5,891,013 A | 4/1999 | Thompson |
| 5,893,878 A | 4/1999 | Pierce |
| 5,899,208 A | 5/1999 | Bonadio |
| 5,906,577 A * | 5/1999 | Beane et al. .................. 600/207 |
| 5,941,890 A | 8/1999 | Voegele et al. |
| 5,946,280 A | 8/1999 | Ohkubo |
| 5,947,922 A | 9/1999 | MacLeod |
| 5,957,913 A | 9/1999 | de la Torre et al. |
| 5,971,995 A | 10/1999 | Rousseau |
| 5,977,431 A | 11/1999 | Knapp et al. |
| 5,990,382 A | 11/1999 | Fox |
| 5,997,515 A | 12/1999 | de la Torre et al. |
| 6,007,561 A | 12/1999 | Bourque et al. |
| 6,024,736 A | 2/2000 | de la Torre et al. |
| 6,033,428 A | 3/2000 | Sardella |
| RE36,702 E | 5/2000 | Green et al. |
| 6,056,766 A | 5/2000 | Thompson et al. |
| 6,066,090 A | 5/2000 | Yoon |
| 6,074,419 A | 6/2000 | Healy et al. |
| 6,077,288 A | 6/2000 | Shimomura et al. |
| 6,080,174 A | 6/2000 | Dubrul et al. |
| 6,086,603 A | 7/2000 | Termin et al. |
| 6,093,141 A | 7/2000 | Mosseri et al. |
| 6,110,154 A | 8/2000 | Shimomura et al. |
| 6,120,513 A | 9/2000 | Bailey et al. |
| 6,123,689 A | 9/2000 | To et al. |
| 6,126,671 A | 10/2000 | Richards et al. |
| 6,132,385 A | 10/2000 | Vain |
| 6,142,396 A | 11/2000 | Gallus |
| 6,142,936 A | 11/2000 | Beane et al. |
| 6,149,642 A | 11/2000 | Gerhart et al. |
| 6,156,184 A | 12/2000 | Antonucci et al. |
| 6,159,200 A | 12/2000 | Verdura et al. |
| 6,162,196 A | 12/2000 | Hart et al. |
| 6,165,184 A | 12/2000 | Verdura et al. |
| 6,171,282 B1 | 1/2001 | Ragsdale |
| 6,197,034 B1 | 3/2001 | Gvozdic et al. |
| 6,217,555 B1 | 4/2001 | Hart et al. |
| 6,220,248 B1 | 4/2001 | Voegele et al. |
| 6,228,055 B1 | 5/2001 | Foerster et al. |
| 6,245,052 B1 | 6/2001 | Orth et al. |
| 6,258,069 B1 | 7/2001 | Carpentier et al. |
| 6,258,102 B1 | 7/2001 | Pagedas |
| 6,261,302 B1 | 7/2001 | Voegele et al. |
| 6,262,196 B1 | 7/2001 | Mecking |
| 6,264,599 B1 | 7/2001 | Slater et al. |
| 6,277,064 B1 | 8/2001 | Yoon |
| 6,290,705 B1 | 9/2001 | Chan et al. |
| 6,293,966 B1 | 9/2001 | Frantzen |
| 6,315,770 B1 | 11/2001 | de la Torre et al. |
| 6,319,246 B1 | 11/2001 | de la Torre et al. |
| 6,325,812 B1 | 12/2001 | Dubrul et al. |
| 6,347,940 B1 | 2/2002 | Gordils Wallis et al. |
| 6,348,034 B1 | 2/2002 | Thompson |
| 6,352,503 B1 | 3/2002 | Matsui et al. |
| 6,425,903 B1 | 7/2002 | Voegele |
| 6,440,061 B1 | 8/2002 | Wenner et al. |
| 6,440,063 B1 | 8/2002 | Beane et al. |
| 6,447,443 B1 | 9/2002 | Keogh et al. |
| 6,447,489 B1 | 9/2002 | Peterson |
| 6,454,783 B1 | 9/2002 | Piskun |
| 6,458,077 B1 | 10/2002 | Boebel et al. |
| 6,471,714 B1 | 10/2002 | Kim |
| 6,485,467 B1 | 11/2002 | Crook et al. |
| 6,488,620 B1 | 12/2002 | Segermark et al. |
| 6,551,270 B1 | 4/2003 | Bimbo et al. |
| 6,551,282 B1 | 4/2003 | Exline et al. |
| 6,578,577 B2 | 6/2003 | Bonadio et al. |
| 6,579,304 B1 | 6/2003 | Hart et al. |
| 6,589,167 B1 | 7/2003 | Shimomura et al. |
| 6,605,063 B2 | 8/2003 | Bousquet |
| 6,623,426 B2 | 9/2003 | Bonadio et al. |
| 6,634,883 B2 | 10/2003 | Ranalli |
| 6,669,674 B1 | 12/2003 | Macoviak et al. |
| 6,702,787 B2 | 3/2004 | Racenet et al. |
| 6,706,033 B1 | 3/2004 | Martinez et al. |

| Patent/Publication | Date | Name |
|---|---|---|
| 6,706,050 B1 | 3/2004 | Giannadakis |
| 6,725,083 B1 | 4/2004 | Burbank et al. |
| 6,764,473 B2 | 7/2004 | Morton |
| 6,766,186 B1 | 7/2004 | Hoyns et al. |
| 6,810,880 B1 | 11/2004 | Jennings, Jr. et al. |
| 6,821,247 B2 | 11/2004 | Vierra et al. |
| 6,846,287 B2 | 1/2005 | Bonadio et al. |
| 6,908,430 B2 | 6/2005 | Caldwell et al. |
| 6,939,296 B2 | 9/2005 | Ewers et al. |
| 6,945,932 B1 | 9/2005 | Caldwell et al. |
| 6,972,026 B1 | 12/2005 | Caldwell et al. |
| 6,994,712 B1 | 2/2006 | Fisher et al. |
| 7,008,377 B2 | 3/2006 | Beane et al. |
| 7,011,314 B2 | 3/2006 | McFarlane |
| 7,014,628 B2 | 3/2006 | Bousquet |
| 7,047,063 B2 | 5/2006 | Burbank et al. |
| 7,052,454 B2 | 5/2006 | Taylor |
| 7,083,576 B2 | 8/2006 | Zarins et al. |
| 7,083,626 B2 * | 8/2006 | Hart et al. .................... 606/108 |
| 7,118,528 B1 | 10/2006 | Piskun |
| 7,163,510 B2 | 1/2007 | Kahle et al. |
| 7,163,525 B2 | 1/2007 | Franer |
| 7,214,185 B1 | 5/2007 | Rosney et al. |
| 7,229,408 B2 | 6/2007 | Douglas et al. |
| 7,311,661 B2 | 12/2007 | Heinrich |
| 7,338,473 B2 | 3/2008 | Campbell et al. |
| 7,344,547 B2 | 3/2008 | Piskun |
| 7,371,227 B2 | 5/2008 | Zeiner |
| 7,393,322 B2 | 7/2008 | Wenchell |
| 7,416,533 B2 | 8/2008 | Gellman et al. |
| 7,438,702 B2 | 10/2008 | Hart et al. |
| 7,449,011 B2 | 11/2008 | Wenchell et al. |
| 7,481,795 B2 | 1/2009 | Thompson et al. |
| 7,585,288 B2 | 9/2009 | Haberland et al. |
| 7,837,612 B2 | 11/2010 | Gill et al. |
| 7,850,600 B1 | 12/2010 | Piskun |
| 7,951,076 B2 * | 5/2011 | Hart et al. .................... 600/206 |
| 7,967,791 B2 * | 6/2011 | Franer et al. ............ 604/167.06 |
| 7,998,068 B2 | 8/2011 | Bonadio et al. |
| 2001/0034528 A1 | 10/2001 | Foerster et al. |
| 2001/0053510 A1 | 12/2001 | Ranalli |
| 2002/0007112 A1 | 1/2002 | Rupp et al. |
| 2002/0026201 A1 | 2/2002 | Foerster et al. |
| 2002/0038179 A1 | 3/2002 | Tschernoster et al. |
| 2002/0103434 A1 | 8/2002 | Swanbom |
| 2002/0156432 A1 | 10/2002 | Racenet et al. |
| 2002/0193815 A1 | 12/2002 | Foerster et al. |
| 2003/0028179 A1 | 2/2003 | Piskun |
| 2003/0113540 A1 | 6/2003 | Anderson et al. |
| 2003/0139756 A1 | 7/2003 | Brustad |
| 2003/0206860 A1 | 11/2003 | Bleyer et al. |
| 2003/0216770 A1 | 11/2003 | Persidsky et al. |
| 2003/0225420 A1 | 12/2003 | Wardle |
| 2004/0015185 A1 | 1/2004 | Ewers et al. |
| 2004/0019322 A1 | 1/2004 | Hoffmann |
| 2004/0024304 A1 | 2/2004 | Foerster et al. |
| 2004/0082969 A1 | 4/2004 | Kerr |
| 2004/0106942 A1 | 6/2004 | Taylor et al. |
| 2004/0106986 A1 | 6/2004 | Andersson et al. |
| 2004/0117032 A1 | 6/2004 | Roth |
| 2004/0138528 A1 | 7/2004 | Richter et al. |
| 2004/0147933 A1 | 7/2004 | McGovern |
| 2004/0199121 A1 | 10/2004 | Wenchell et al. |
| 2004/0215063 A1 | 10/2004 | Bonadio et al. |
| 2004/0230160 A1 | 11/2004 | Blanco |
| 2004/0230161 A1 | 11/2004 | Zeiner |
| 2004/0254426 A1 | 12/2004 | Wenchell |
| 2005/0020884 A1 | 1/2005 | Hart et al. |
| 2005/0033342 A1 | 2/2005 | Hart et al. |
| 2005/0085842 A1 | 4/2005 | Eversull et al. |
| 2005/0137609 A1 | 6/2005 | Guiraudon |
| 2005/0148823 A1 | 7/2005 | Vaugh et al. |
| 2005/0155611 A1 | 7/2005 | Vaugh et al. |
| 2005/0192483 A1 | 9/2005 | Bonadio et al. |
| 2005/0209608 A1 | 9/2005 | O'Heeron |
| 2005/0215862 A1 | 9/2005 | Larson et al. |
| 2005/0216028 A1 * | 9/2005 | Hart et al. .................... 606/108 |
| 2005/0222582 A1 | 10/2005 | Wenchell |
| 2005/0229501 A1 | 10/2005 | Grossman et al. |
| 2005/0267419 A1 | 12/2005 | Smith |
| 2005/0273132 A1 | 12/2005 | Shluzas et al. |
| 2005/0277946 A1 | 12/2005 | Greenhalgh |
| 2006/0012965 A1 | 1/2006 | Beall et al. |
| 2006/0019592 A1 | 1/2006 | Kupferberg et al. |
| 2006/0019723 A1 | 1/2006 | Vorenkamp et al. |
| 2006/0020241 A1 | 1/2006 | Piskun et al. |
| 2006/0020281 A1 | 1/2006 | Smith |
| 2006/0021061 A1 | 1/2006 | Cerri et al. |
| 2006/0021891 A1 | 2/2006 | Franer et al. |
| 2006/0025813 A1 | 2/2006 | Shelton et al. |
| 2006/0030755 A1 | 2/2006 | Ewers et al. |
| 2006/0071432 A1 | 4/2006 | Staudner |
| 2006/0129165 A1 | 6/2006 | Edoga et al. |
| 2006/0149137 A1 | 7/2006 | Pingleton et al. |
| 2006/0161050 A1 * | 7/2006 | Butler et al. .................... 600/208 |
| 2006/0212061 A1 | 9/2006 | Wenchell |
| 2006/0212062 A1 | 9/2006 | Farascioni |
| 2006/0217665 A1 | 9/2006 | Prosek |
| 2006/0224129 A1 | 10/2006 | Beasley et al. |
| 2006/0224164 A1 | 10/2006 | Hart et al. |
| 2006/0229501 A1 | 10/2006 | Jensen et al. |
| 2006/0241651 A1 | 10/2006 | Wilk |
| 2006/0241671 A1 | 10/2006 | Greenhalgh |
| 2006/0247498 A1 | 11/2006 | Bonadio et al. |
| 2006/0247499 A1 | 11/2006 | Butler et al. |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh et al. |
| 2006/0258899 A1 | 11/2006 | Gill et al. |
| 2006/0264706 A1 | 11/2006 | Piskun |
| 2006/0270911 A1 | 11/2006 | Voegele et al. |
| 2007/0049966 A1 | 3/2007 | Bonadio et al. |
| 2007/0060939 A1 | 3/2007 | Lancial et al. |
| 2007/0085232 A1 | 4/2007 | Brustad et al. |
| 2007/0088202 A1 | 4/2007 | Albrecht et al. |
| 2007/0088204 A1 | 4/2007 | Albrecht et al. |
| 2007/0088258 A1 | 4/2007 | Wenchell et al. |
| 2007/0088277 A1 | 4/2007 | McGinley et al. |
| 2007/0118021 A1 | 5/2007 | Pokorney |
| 2007/0118175 A1 | 5/2007 | Butler et al. |
| 2007/0151566 A1 | 7/2007 | Kahle et al. |
| 2007/0185453 A1 | 8/2007 | Michael et al. |
| 2007/0208312 A1 | 9/2007 | Norton et al. |
| 2007/0255219 A1 | 11/2007 | Vaugh et al. |
| 2008/0009797 A1 | 1/2008 | Stellon et al. |
| 2008/0025519 A1 | 1/2008 | Yu et al. |
| 2008/0027476 A1 | 1/2008 | Piskun |
| 2008/0051739 A1 | 2/2008 | McFarlane |
| 2008/0058728 A1 | 3/2008 | Soltz et al. |
| 2008/0065021 A1 | 3/2008 | Jenkins et al. |
| 2008/0086080 A1 | 4/2008 | Mastri et al. |
| 2008/0119821 A1 | 5/2008 | Agnihotri et al. |
| 2008/0132765 A1 | 6/2008 | Beckman et al. |
| 2008/0183044 A1 | 7/2008 | Colleran et al. |
| 2008/0255519 A1 | 10/2008 | Piskun et al. |
| 2008/0281161 A1 | 11/2008 | Albrecht et al. |
| 2009/0005799 A1 | 1/2009 | Franer et al. |
| 2009/0012477 A1 | 1/2009 | Norton et al. |
| 2009/0036738 A1 | 2/2009 | Cuschieri et al. |
| 2009/0076555 A1 | 3/2009 | Lowry et al. |
| 2009/0082731 A1 | 3/2009 | Moreno |
| 2009/0118587 A1 | 5/2009 | Voegele et al. |
| 2009/0187079 A1 | 7/2009 | Albrecht et al. |
| 2009/0270685 A1 | 10/2009 | Moreno et al. |
| 2009/0270686 A1 | 10/2009 | Duke et al. |
| 2009/0270818 A1 | 10/2009 | Duke |
| 2010/0010310 A1 | 1/2010 | Weisenburgh, II et al. |
| 2010/0081863 A1 | 4/2010 | Hess et al. |
| 2010/0081864 A1 | 4/2010 | Hess et al. |
| 2010/0081871 A1 | 4/2010 | Widenhouse et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |
| 2010/0228090 A1 | 9/2010 | Weisenburgh, II et al. |

| | | | |
|---|---|---|---|
| 2010/0228091 A1 | 9/2010 | Widenhouse et al. | |
| 2010/0228092 A1 | 9/2010 | Ortiz et al. | |
| 2010/0228094 A1 | 9/2010 | Ortiz et al. | |
| 2010/0228096 A1 | 9/2010 | Weisenburgh, II et al. | |
| 2010/0228198 A1 | 9/2010 | Widenhouse et al. | |
| 2010/0240960 A1 | 9/2010 | Richard | |
| 2010/0249525 A1 | 9/2010 | Shelton, IV et al. | |
| 2010/0261970 A1 | 10/2010 | Shelton, IV et al. | |
| 2010/0261972 A1 | 10/2010 | Widenhouse et al. | |
| 2010/0261974 A1 | 10/2010 | Shelton, IV et al. | |
| 2010/0262080 A1 | 10/2010 | Shelton, IV et al. | |
| 2010/0268162 A1 | 10/2010 | Shelton, IV et al. | |
| 2010/0274093 A1 | 10/2010 | Shelton, IV | |
| 2010/0280327 A1 | 11/2010 | Nobis et al. | |
| 2010/0312060 A1 | 12/2010 | Widenhouse et al. | |
| 2010/0312061 A1 | 12/2010 | Hess et al. | |
| 2010/0312062 A1 | 12/2010 | Cropper et al. | |
| 2010/0312063 A1 | 12/2010 | Hess et al. | |
| 2010/0312064 A1 | 12/2010 | Weisenburgh, II et al. | |
| 2010/0312065 A1 | 12/2010 | Shelton, IV et al. | |
| 2010/0312066 A1 | 12/2010 | Cropper et al. | |
| 2010/0312189 A1 | 12/2010 | Shelton, IV et al. | |

FOREIGN PATENT DOCUMENTS

| | | | |
|---|---|---|---|
| DE | 19814576 A1 | 10/1999 | |
| DE | 20022005 U1 | 4/2001 | |
| EP | 0568383 | 11/1993 | |
| EP | 568383 A1 | 11/1993 | |
| EP | 0577400 A1 | 1/1994 | |
| EP | 577400 A1 | 1/1994 | |
| EP | 0637431 A1 | 2/1995 | |
| EP | 0646358 | 4/1995 | |
| EP | 646358 A1 | 4/1995 | |
| EP | 709918 | 5/1996 | |
| EP | 0776231 B1 | 6/1997 | |
| EP | 950376 | 10/1999 | |
| EP | 0950376 A1 | 10/1999 | |
| EP | 0966924 A1 | 12/1999 | |
| EP | 0996925 A1 | 5/2000 | |
| EP | 1219251 A1 | 7/2002 | |
| EP | 1219252 A1 | 7/2002 | |
| EP | 1219253 A1 | 7/2002 | |
| EP | 1350476 | 10/2003 | |
| EP | 1702575 A2 | 9/2006 | |
| EP | 1731105 A1 | 12/2006 | |
| EP | 1774918 A1 | 4/2007 | |
| EP | 2119404 A1 | 11/2009 | |
| FR | 2710270 | 3/1995 | |
| FR | 2710270 A1 | 3/1995 | |
| JP | 2000033089 A | 2/2000 | |
| JP | 2006320750 | 11/2006 | |
| WO | 9407552 A1 | 4/1994 | |
| WO | 9602297 A1 | 2/1996 | |
| WO | 9608208 A1 | 3/1996 | |
| WO | 9608897 A1 | 3/1996 | |
| WO | 9636283 A1 | 11/1996 | |
| WO | 9729709 A1 | 8/1997 | |
| WO | 9735521 A1 | 10/1997 | |
| WO | 9743958 A1 | 11/1997 | |
| WO | 9810712 A1 | 3/1998 | |
| WO | 9903536 A1 | 1/1999 | |
| WO | 0030592 A1 | 6/2000 | |
| WO | 0032253 A1 | 6/2000 | |
| WO | 0032263 A1 | 6/2000 | |
| WO | 0041759 A1 | 7/2000 | |
| WO | 0108563 A2 | 2/2001 | |
| WO | 0217800 A2 | 3/2002 | |
| WO | 0239890 A2 | 5/2002 | |
| WO | 0239918 A1 | 5/2002 | |
| WO | 02058543 A2 | 8/2002 | |
| WO | 02094133 A1 | 11/2002 | |
| WO | 03005890 A2 | 1/2003 | |
| WO | 03077730 A2 | 9/2003 | |
| WO | 2004030515 A2 | 4/2004 | |
| WO | 200500454 A1 | 1/2005 | |
| WO | 2005002454 A1 | 1/2005 | |
| WO | 2005087112 A1 | 9/2005 | |
| WO | 2005094432 A2 | 10/2005 | |
| WO | 2005097019 A2 | 10/2005 | |
| WO | 2005097234 A2 | 10/2005 | |
| WO | 2006057982 A2 | 6/2006 | |
| WO | 2006110733 A2 | 10/2006 | |
| WO | 2007008741 A1 | 1/2007 | |
| WO | 2007119232 A2 | 10/2007 | |
| WO | 2008012787 A2 | 1/2008 | |
| WO | 2008024502 A2 | 2/2008 | |
| WO | 2008028149 A2 | 3/2008 | |
| WO | 2008121294 A1 | 10/2008 | |
| WO | 2009035663 A2 | 3/2009 | |

OTHER PUBLICATIONS

International Search Report, from PCT/US10/36829, mailed Sep. 9, 2010 (5 pages).
European Search Report, EP 10250732, dated Jul. 28, 2010.
International Search Report and Written Opinion for Application No. PCT/US2010/037190, dated Sep. 22, 2010 (15 pages).
"Surgeon performs single-port laparoscopic surgery > Kidney removal with instructions inserted through single port access SPA > One Port Umbilicus Surgery OPUS > Uretero-pelvic junction repair > Bilateral pyeloplasy > Triport > Quadport > R-Port laparoscopic access device > Advanced Surgical Concepts ASC" Ideas for Surgery.com, Dec. 2007, 4 pages.
Desai, Mihir M. et al., "Laparoscopic and Robtic Urology-Scarless single port transumbilical nephrectomy and pyeloplasty: first clinical report," Journal Compilation, 2008 BJU International, 101, pp. 83-88.
Lee D, et al. Novel Approach to Minimizing Trocar Sites during Challenging Hand-Assisted Laparoscopic Surgery Utilizing the GelPort: Trans-Gel Instrument and Utilization, Journal of Endourology, vol. 17, No. 2, Mar. 2003, pp. 69-71.
Nakajima K, et al. Hand-assisted laparoscopic colorectal surgery using GelPort, Surg Endosc. Jan. 2004; 18(1)102-5. Epub Sep. 10, 2003.
Nakajima K, et al. Use of the surgical towel in colorectal hand-assisted laparoscopic surgery (HALS), Surg Endosc. Mar. 2004; 18(3):552-3.
Patel, R. et al. "Hand-Assisted Laparoscopic Devices: The Second Generation," Journal of Endourology, vol. 18, No. 7, Sep. 2004, pp. 649-653.
Rane, A. et al., "Single-Port Access Nephrectomy and Other Laparoscopic Urologic Procedures Using a Novel Laparoscopic Port (R-Port)," Urology, Aug. 2008; 72(2):260-264.
International Search Report and Written Opinion for Application No. PCT/US2010/036806, dated Sep. 3, 2010 (8 pages).
International Search Report and Written Opinion for Application No. PCT/US2010/036820, dated Oct. 22, 2010 (18 pages).
U.S. Appl. No. 12/712,276, filed Feb. 25, 2010, Access Device.
U.S. Appl. No. 12/712,402, filed Feb. 25, 2010, Method of Surgical Access.
U.S. Appl. No. 12/712,391, filed Feb. 25, 2010, Access Method With Insert.
U.S. Appl. No. 12/712,403, filed Feb. 25, 2010, Access Device Including Retractor and Insert.

* cited by examiner

DEVICES AND METHODS FOR PROVIDING ACCESS INTO A BODY CAVITY

CROSS-REFERENCE TO RELATED APPLICATIONS

The present application claims priority to U.S. Provisional Application No. 61/165,080 entitled "Access Device" filed Mar. 31, 2009, which is hereby incorporated by reference in its entirety.

FIELD OF THE INVENTION

The present invention relates to methods and devices for providing surgical access into a body cavity.

BACKGROUND OF THE INVENTION

Abdominal laparoscopic surgery gained popularity in the late 1980's, when benefits of laparoscopic removal of the gallbladder over traditional (open) operation became evident. Reduced post-operative recovery time, markedly decreased post-operative pain and wound infection, and improved cosmetic outcome are well established benefits of laparoscopic surgery, derived mainly from the ability of laparoscopic surgeons to perform an operation utilizing smaller incisions of the body wall.

Laparoscopic procedures typically involve inserting a surgical access device, such as a straight tubular cannula or trocar sleeve, into the abdominal cavity. Insufflation of the abdominal cavity with carbon dioxide gas to a pressure of around 15 mm Hg is generally used to increase the interior space for the surgical procedure. Accordingly, various sealing elements are used within the trocar sleeve to seal its working channel both before and after a surgical instrument is inserted through the trocar sleeve to seal the body cavity from the outside in order to achieve and maintain insufflation. Suitable laparoscopic instruments (graspers, dissectors, scissors, retractors, etc.) can be placed through the one or more trocar sleeves depending on the procedure and needs of the surgeon. Surgeons can then perform a variety of diagnostic procedures, such as visual inspection or removal of a tissue sample for biopsy, or treatment procedures, such as removal of a polyp or tumor or restructuring tissue.

Because of the rise in popularity of minimally invasive surgeries, there has been significant development with respect to the procedures and the instruments used in laparoscopic procedures. For example, in some procedures a single incision at the navel can be sufficient to provide access to a surgical site. This is because the umbilicus can be a preferred way to access an abdominal cavity in a laparoscopic procedure. The umbilical incision can be easily enlarged without significantly compromising cosmesis and without significantly increasing the chances of wound complications, thus allowing multiple instruments to be introduced through a single access device placed in an incision.

Current devices used in single site laparoscopic procedures generally provide a plurality of seals in order to simultaneously accommodate a plurality of surgical instruments. Seals are typically disposed within the access device at the level of the abdomen wall or are fixed to the access device well above the body wall. As a result, the range of motion of the seals is limited by the access device, thereby vastly restricting the quadrant-to-quadrant reach of surgical instruments inserted therethrough. Seals that extend below the access device but fail to extend through the abdomen wall are subject to collapse as the incision itself closes in around the seal and prevents insertion of a surgical instrument through the seal.

Accordingly, there remains a need for methods and devices that provide instrument range-of-motion without subjecting the seal to collapse by the incision.

SUMMARY OF THE INVENTION

The present invention provides methods and devices for accessing a body cavity. In general, a surgical access device is provided that can include a retractor that forms a working channel through tissue, a seal housing for sealing the working channel and/or forming a seal around an instrument inserted therethrough, and a suspension member or tether configured to suspend the seal housing within the body cavity.

In one exemplary embodiment, the seal housing can be suspended within the working channel of the retractor by a flexible tether coupled to the retractor such that at least a portion of the seal housing can extend distally beyond the distal end of the retractor and can be angularly oriented relative to the retractor. The seal housing can form a seal across the working channel of the retractor, and can include one or more sealing elements disposed therein that seal the working channel and/or form a seal around an instrument that is inserted through the sealing element.

The suspension member or tether can have various configurations. In one embodiment, the flexible tether can include a proximal housing that is rotatably coupled to a retractor housing on the flexible retractor. In another embodiment, the flexible tether can include a proximal flange that rests against the proximal end of the retractor. A distal portion of the retractor extending from the housing or flange can be flexible and it can include features for seating the seal housing. For example, the distal portion of the flexible tether can include an engagement feature, such as an annular rim or flange, or a sleeve, configured to removably engage the seal housing.

In another embodiment, the surgical access device can include a retractor having proximal and distal ends with a working channel extending therethrough. The proximal end can be configured to be positioned adjacent to an external surface of a patient's tissue and the distal end can be configured to extend into a body cavity such that the working channel provides a pathway through the tissue. The access device can also include a suspension member having a proximal portion configured to couple to the proximal end of the retractor and a distal portion that extends through the working channel of the retractor. A seal housing can be disposed within the distal portion of the suspension member and it can have at least one sealing element disposed therein and configured to form a seal around an instrument disposed therethrough. At least a portion of the suspension member can be flexible to allow the seal housing to extend beyond the distal end of the retractor.

The retractor can also have any number of configurations, shapes, and sizes. In one embodiment, the retractor can be a hollow flexible cylindrical member having a mid-portion with a maximum diameter that is less than a maximum diameter of the proximal and distal ends of the retractor. The mid-portion can be configured to be positioned within an opening in tissue and the proximal and distal ends can be configured to engage the tissue therebetween.

The suspension member or tether can have any number of configurations, shapes, and sizes and can be formed of any number of materials. In one embodiment, the proximal portion of the suspension member or tether can include a radially-outward extending flange that is configured to rest against the proximal end of the retractor. In another embodiment, the proximal portion of the suspension member or tether can include a collar that is mated to a housing on the proximal end of the retractor. The distal portion of the suspension member or tether can also have various configurations, but in one embodiment is in the form of a flexible sleeve. The distal end of the flexible sleeve can include various features for engaging the seal housing. In one embodiment, the distal portion of the suspension member can include an engagement feature that can removably engage the seal housing. The engagement feature can be, for example, an annular member or rim that can engage the seal housing or retain the seal housing within the distal portion of the suspension member.

The seal housing can also have any number of configurations, shapes, and sizes and it can be formed of any number of materials. In an exemplary embodiment, the seal housing is configured to form a seal across the working channel of the retractor. The seal housing can contain one or more sealing elements that are configured to form a seal around an instrument and/or seal the working channel.

In another embodiment, a method for accessing a body cavity is provided that can include positioning a flexible retractor within tissue such that a working channel of the flexible retractor forms a pathway through the tissue and into a body cavity. The method can also include inserting a surgical instrument through a sealing element in a seal housing suspended within the body cavity by a flexible tether that extends between the seal housing and a proximal portion of the flexible retractor to position a distal end of the surgical instrument in the body cavity. The surgical instrument can be manipulated to cause the seal housing to move relative to the flexible retractor, and thereby cause the flexible tether to flex. The flexible tether and seal housing can be removed from the retractor such that the retractor is left disposed within the tissue. A second surgical instrument can also be inserted through a second sealing element in the seal housing to position a distal end of the second surgical instrument in the body cavity.

BRIEF DESCRIPTION OF DRAWINGS

This invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment can be combined with the features of other embodiments. Such modifications and variations are intended to be included within the scope of the present invention.

Various exemplary methods and devices are provided for accessing a body cavity. In general, the access devices and methods described herein can be used in minimally-invasive surgeries such as laparoscopic surgeries, and can provide improved range of motion of surgical instruments used therewith. The devices can have a number of different configurations, but in certain exemplary embodiments, an access device can generally include a retractor configured to form a working channel through tissue and into a body cavity, a seal housing having at least one seal therein for sealing the working channel and/or forming a seal around an instrument inserted therethrough, and a suspension member or tether configured to suspend the seal housing within the body cavity. In use, one or more surgical instruments can be inserted through the seal(s) in the seal housing, and thus through the working channel of the retractor, to position a distal end of the surgical instrument(s) in the body cavity. The suspension member can allow the seal housing to move and/or angularly diverge relative to the retractor. Such free floating movement of the suspension member allows a sealing engagement to be maintained between a seal and an instrument inserted through the seal. A person skilled in the art will appreciate that the access devices can be used in any surgical procedure, including open procedures, and can have a variety of other configurations and include various other features known in the art. Moreover, the suspension members disclosed herein can be used in a variety of other devices to suspend a housing to allow for free angular orientation of the housing.

Figure 1:
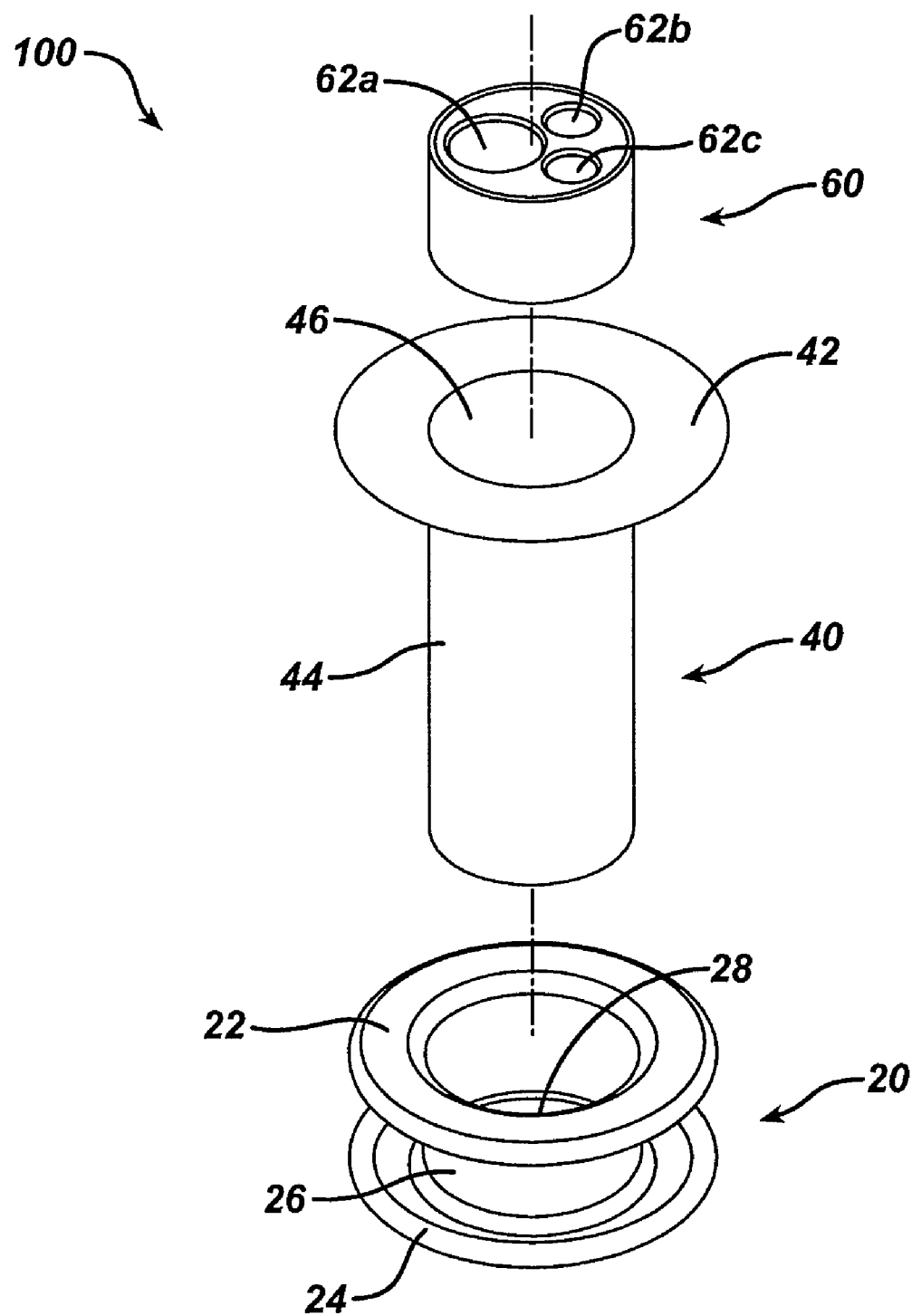
FIG. 1 is an exploded perspective view of one exemplary embodiment of a surgical access device.
Figure 2:
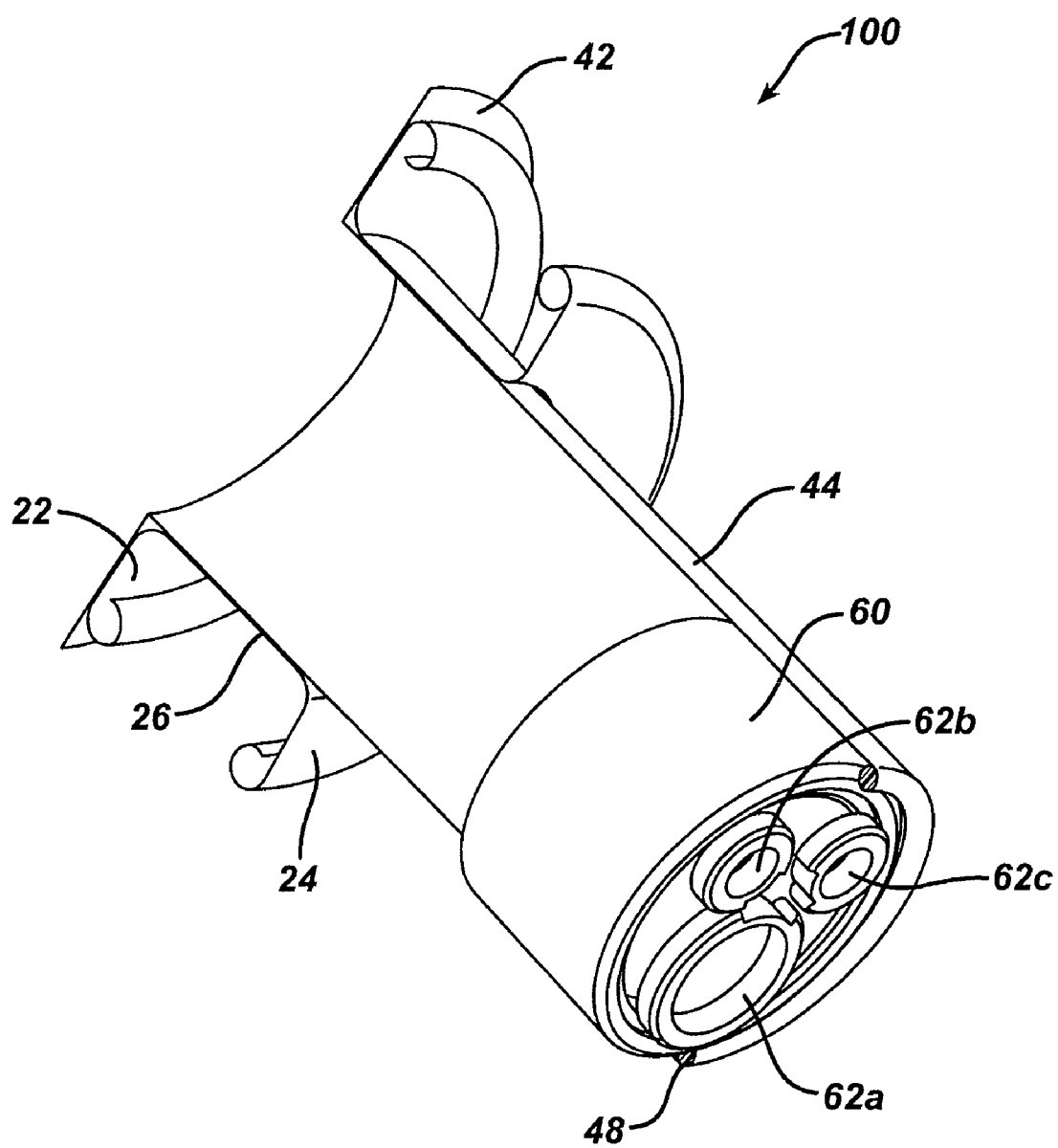
FIG. 2 is a perspective cross-sectional view of the assembled device of FIG. 1.
Figure 3:
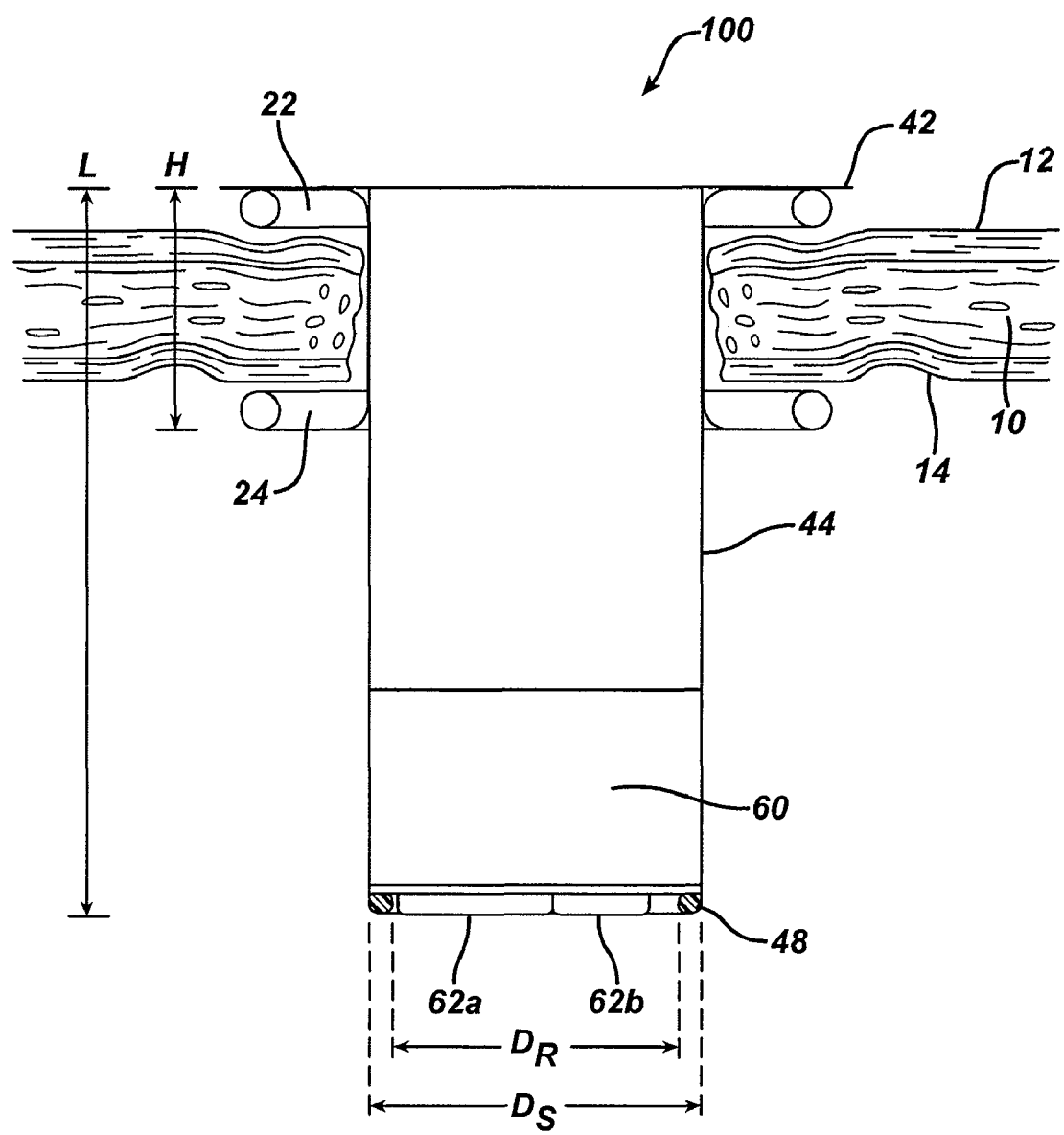
FIG. 3 is a side cross-sectional view of the device of FIG. 2 disposed in a tissue opening.

FIGS. 1-3 illustrate one exemplary embodiment of a surgical access device 100 having a retractor 20, seal housing 60, and suspension member or tether 40. In general, the retractor 20 is configured to be disposed within tissue to form a working channel 28 through the tissue and into the body cavity, and the suspension member 40 can be seated within the working channel 28 of the retractor 20 for retaining the seal housing 60 at a location distal of a distal end of the retractor 20 such that the seal housing 60 is suspended within the body cavity. At least a portion of the suspension member 40 can be flexible to allow the seal housing 60 to be oriented at various angular orientations relative to the retractor 20.

One skilled in the art will appreciate that the retractor 20 can have any number of configurations, shapes, and sizes depending at least in part on the size of the incision or opening in which the retractor will be disposed, the surgical components with which it will be used, and the type of surgical procedure with which it will be used. Although generally referred to as a retractor herein, the retractor 20 of the various surgical access devices and methods described herein can be a wound protector, cannula, ring retractor, or any other member configured to form a pathway through tissue. The retractor 20 can provide access to an interior surgical site within a body cavity and can include proximal and distal ends and a working channel 28 extending therebetween. In an exemplary embodiment, the retractor 20 is positioned within an opening in tissue such that the distal end of the retractor 20 extends into a patient's body cavity or is adjacent to an inner surface of the tissue and the proximal end is positioned adjacent to the patient's skin on an exterior surface of the patient's body. The working channel 28 provides a pathway through the tissue through which surgical instruments can be inserted from outside the body to the interior body cavity. The retractor 20 can be placed in any opening within a patient's body, whether a natural orifice or an opening made by an incision. For example, the retractor 20 can be placed through the umbilicus, vaginally, or percutaneously.

In one exemplary embodiment, as depicted in FIGS. 1-3, the retractor 20 includes a proximal flange 22, a distal flange 24, and a cylindrical mid-portion 26 extending therebetween. The proximal and distal flanges 22, 24 can extend radially-outward relative to a longitudinal axis of the mid-portion 26 such that the flanges 22, 24 have an increased diameter relative to the mid-portion. As shown in FIG. 3, when the retractor 20 is positioned in tissue, the proximal flange 22 can be disposed external to a body wall 10 and can engage the outer surface 12 of the patient's skin, the distal flange 24 can be disposed within the patient, such as within the patient's abdominal cavity and can engage an inner surface 14 of the patient's body wall 10 when positioned during surgery, and the mid-portion 26 can be disposed within the tissue wall.

The proximal and distal ends of the retractor 20 can have any suitable configuration that allow the retractor 20 to be secured within the incision. The proximal and distal flanges 22, 24 are depicted as having an annular shape, but they can have any configuration including and without limitation, a circular, oval, elliptical, square, and rectangular configuration. Additionally, the proximal and distal flanges 22, 24 need not be closed or continuous but can, for example, include a plurality of circumferentially-spaced, radially-extending tabs.

As shown in FIGS. 1-3, the cylindrical mid-portion 26 extending between the proximal flange 22 and the distal flange 24 defines a working channel 28 having a circular cross-sectional shape. The external surface of the cylindrical mid-portion 26 can engage at least a portion of the patient's body wall 10 when the retractor 20 is positioned in tissue. The skin's natural elasticity can result in compression of the skin against the external surface of the mid-portion 26 and can further assist in the retention of the retractor 20 in the body opening or incision. Although the working channel 28 can have any cross-sectional shape including and without limitation, circular, oval, elliptical, square, and rectangular, a circular working channel can provide the maximum area per unit of perimeter length. A circular working channel 28 can also provide ease of rotation of the suspension member 40 and/or the seal housing 60 relative to the retractor 20.

The retractor 20 can have a variety of sizes. For non-limiting example, the retractor 20 can have a longitudinal length of between about 2 cm to about 7 cm, a maximum diameter corresponding to diameters of the proximal and distal ends of about 40 mm to about 80 mm, and a working channel diameter of between about 15 mm to about 40 mm. A surgeon can select an appropriately-sized retractor depending on, e.g., the procedure to be performed and the size of the incision. For non-limiting example, a surgeon can select a retractor 20 having a length approximately equal to the thickness of the body wall 10 to assist in maintaining an air-tight seal between the retractor 20 and the body wall 10. It should also be understood that the diameter of the proximal and distal ends can differ such that the distal end of the retractor 20 can have a greater diameter than the proximal end, or vice versa. It should also be understood that the diameter of the working channel 28 need not be constant and can vary along its longitudinal length. In one embodiment, a working channel 28 smaller than that required to permit passage of a user's hand and generally less than about 50 mm can be desirable, so as to provide access for multiple instruments without requiring a relatively large incision. Alternatively, the retractor 20 can have a working channel 28 of sufficient diameter to permit passage of a user's hand.

The retractor 20 can be rigid, semi-rigid, or flexible. More than one material can be used to form the retractor 20, and the retractor 20 can include some portions that are more rigid than others. For example, the retractor 20 can be formed of a resiliently deformable material, such as natural rubber, silicone, or a suitable deformable elastomer or elastomeric material. The retractor 20 can also include some portions that are formed of a stiffer material, such as polyethylene, polycarbonate, polyester, polyetherimide material, or stainless steel. For example, the distal flange 24 of the retractor 20 can be resiliently deformable to ease insertion through an incision while the proximal flange 22 can be relatively stiff to maintain the working channel 28 in a predetermined shape or size. Once the distal flange 24 of the retractor 20 has been inserted into the body cavity, the distal flange 24 can be configured to resiliently return to its undeformed configuration.

One of skill in the art will appreciate that the retractor 20 can include additional features to help secure the retractor 20 within an opening in the body and provide access to an internal body cavity. In some embodiments, at least a portion of the retractor 20 can be configured to form an air-tight seal with a surface of the patient's body wall 10 such that insufflation of the body cavity can be maintained. Additionally, although the distal-facing surface of the proximal flange 22 and the proximal-facing surface of the distal flange 24 are depicted as being substantially flat in FIGS. 1-3, these surfaces can include surface features to help securely engage the retractor 20 to the patient's body wall 10. The retractor 20 can additionally include mating features that allow the suspension member 40 to be fixedly, releasably, and/or movably coupled to the retractor 20. Such mating features can be formed in or extend from the proximal end, distal end, or mid-portion of the retractor 20.

The suspension member 40 can be configured to suspend the seal housing 60 within a body cavity and can generally include a proximal portion configured to couple to the retractor 20 and a distal portion that is configured to extend through the working channel 28 of the retractor 20 and couple to the seal housing 60. The suspension member 40 can have a variety of configurations, but in the embodiment shown in FIGS. 1-3, the proximal portion of the suspension member 40 includes an annular flange 42 that extends radially-outward the distal portion of the suspension member 40, which in the illustrated embodiment is in the form of a cylindrical sleeve 44. The annular flange 42 can have a diameter less than, equal to, or greater than the proximal flange 22 of the retractor 20 and it can have a diameter greater than the diameter of the working channel 28 such that the annular flange 42 abuts or otherwise contacts the proximal end of the retractor 20 when the cylindrical sleeve 44 of the suspension member 40 is inserted through the proximal end of the working channel 28. The flange 42 can act as a stop to prevent the suspension member 40 from passing into or through the working channel 28.

The flange 42 of the proximal portion of the suspension member 40 is depicted having an annular shape but it can have any shape including and without limitation, a circular, oval, elliptical, square, and rectangular shape. Additionally, the flange 42 need not be closed or continuous, but can, for non-limiting example, include a plurality of circumferentially-spaced, radially-extending tabs. One of skill in the art will appreciate that the proximal portion of the suspension member 40 can have any configuration such that the proximal portion of the suspension member 40 can support the distal portion of the suspension member during surgery.

The suspension member 40 can be integral with the retractor 20 (e.g., formed as a single unitary component) or it can be fixedly, removably, and/or movably mated to the retractor 20. As shown in FIGS. 1-3, the distal-facing surface of the flange 42 is configured to abut the proximal flange 22 of the retractor 20 when the suspension member 40 is fully inserted into the retractor 20. The opposing surfaces can be configured to slide relative to one another such that the suspension member 40 can be rotated relative to the retractor 20, or the proximal portion of the suspension member 40 can engage the proximal end of the retractor through surface features or engagement features formed on or extending from either or both of the proximal ends of the suspension member 40 or the retractor 20 to prevent relative rotation. For non-limiting example, the opposing surfaces can be textured to discourage or prevent rotation of the suspension member 40 relative to the retractor 20. One skilled in the art will appreciate that any number of engagement mechanisms (e.g., snap-fit couplings, threading, etc.) can be used to fixedly or removably couple the suspension member 40 to the retractor 20. One skilled in the art will also appreciate that the engagement mechanism can be formed in or extend from any portion of the suspension member 40 or the retractor 20 such that the suspension member 40 can couple to the proximal or distal end of the retractor 20 or any location therebetween.

Figure 4:
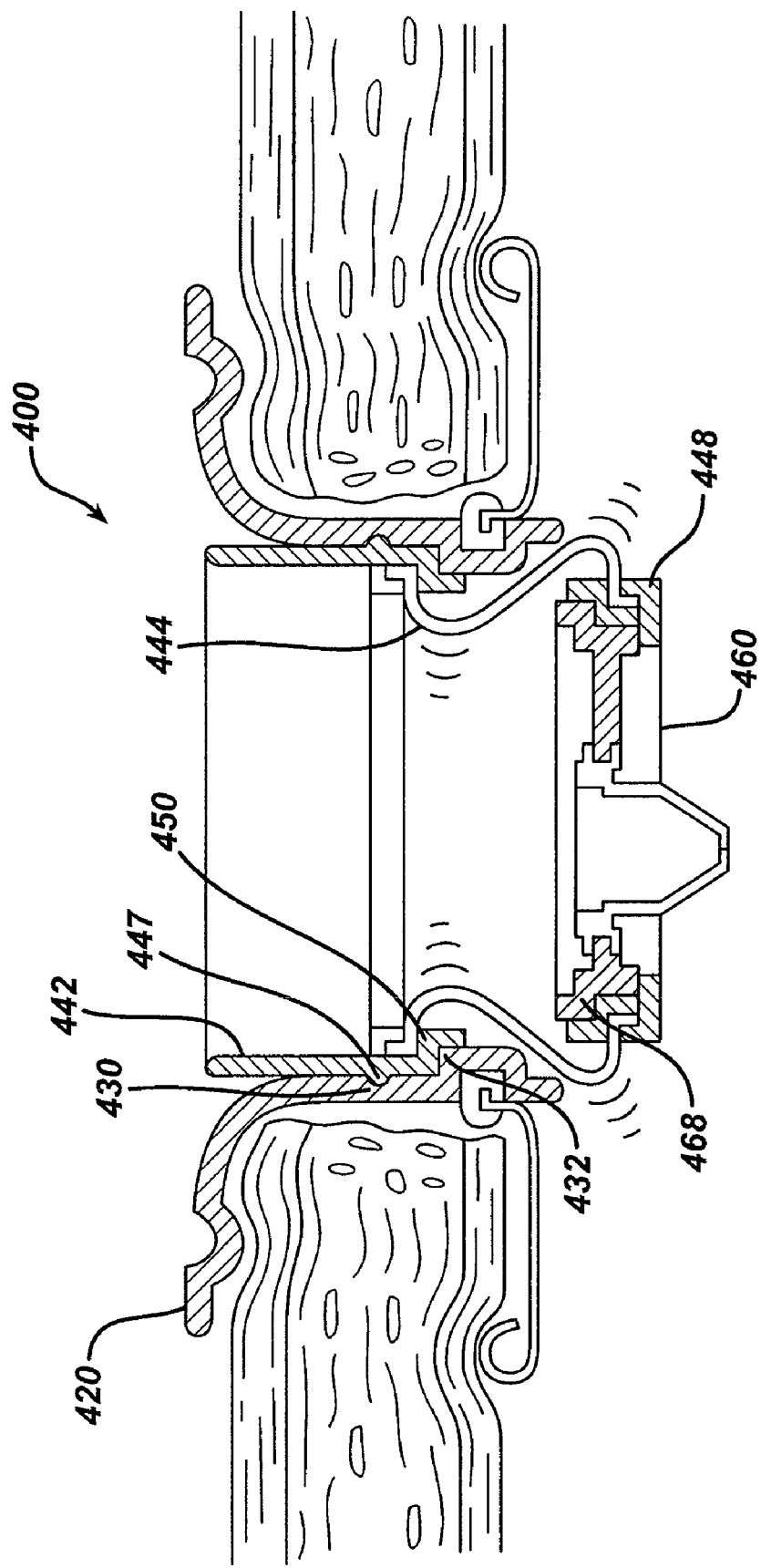
FIG. 4 is a side cross-sectional view of another exemplary embodiment of a surgical access device disposed in an opening formed in tissue.
Figure 5:
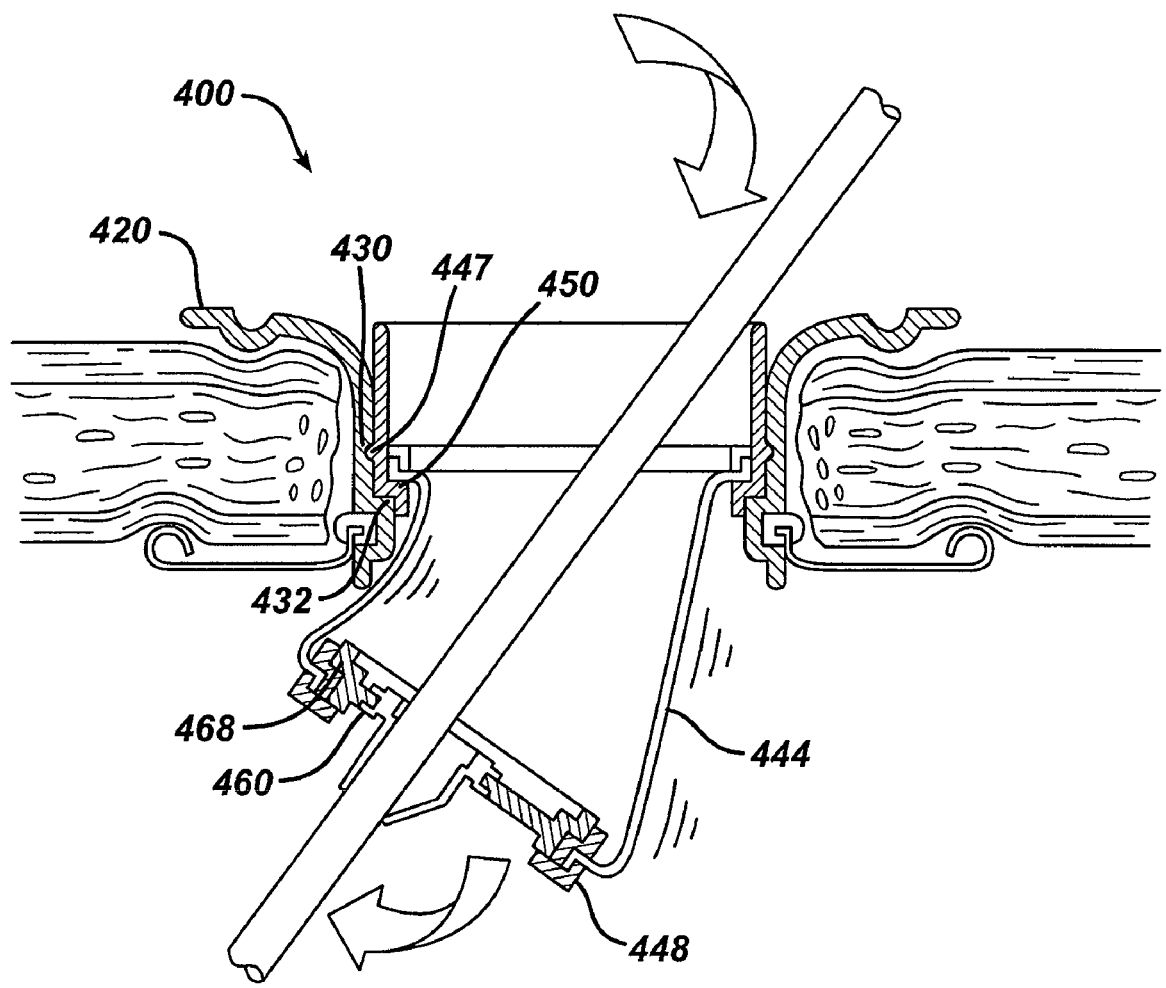
FIG. 5 is a side cross-sectional view of the device of FIG. 4 with a surgical instrument disposed therethrough.

For non-limiting example, in another embodiment depicted in FIGS. 4 and 5, the suspension member or tether of surgical access device 400 does not abut or couple to the proximal end of the retractor 420 as in the embodiment illustrated in FIGS. 1-3, but instead includes a tubular housing 442 that can be configured to be disposed within a working channel of the retractor 420. The tubular member 442 can be coupled to a flexible sleeve 444 which in turn can be coupled to a seal housing 460. The external surface of tubular housing 442 can include an engagement mechanism to engage the retractor 420, e.g., an annular flange 447 of the tubular housing 442 can snap-fit within a corresponding groove 430 formed on an internal surface of the retractor 420. Alternatively, or in addition, a shoulder 450 of the tubular housing 442 can rest on or engage an annular rim 432 formed on an internal surface of the retractor 420. The sleeve 444 can extend through the working channel of the retractor 420 and suspend the seal housing 460 within a body cavity when the surgical access device 400 is positioned in tissue.

Again referring to FIGS. 1-3, the distal portion of the suspension member 40 can include a cylindrical sleeve 44 that extends distally from the flange 42. An inner surface of the sleeve 44 can define a passageway 46 through which surgical instruments can be passed. The sleeve 44 can have a variety of configurations, shapes, and sizes. In the illustrated embodiment, the sleeve 44 has a generally elongate cylindrical shape. However, the sleeve 44 can have various cross-sectional shapes, such as square, ovular, triangular, etc. The size of the sleeve can also vary. In an exemplary embodiment as depicted in FIG. 3, the sleeve 44 can have a length that is sufficient to extend through tissue when disposed in an opening therein, and can have a longitudinal length L that is greater than a height H of the retractor 20 such that the seal housing 60, when disposed within the sleeve 44, can be suspended at a location adjacent or distal to the distal end of the retractor 20. The sleeve 44 can also have an outer diameter that allows the sleeve 44 to be disposed through the working channel 28 of the retractor 20 but is sufficient to retain the seal housing 60 therein. The outer diameter of the sleeve 44 can also be selected such that the outer surface of the sleeve 44 forms a gas-tight seal with at least a portion of the retractor 20 when the sleeve 44 is inserted into the working channel 28. In an exemplary embodiment, the length of the sleeve 44 can be in the range of about 4 cm to about 9 cm and the outer diameter of the sleeve 44 can be in the range of about 60 mm to about 100 mm. The diameter of sleeve 44 need not be constant and can vary along the length of the sleeve 28.

The suspension member 40 can be rigid, semi-rigid, or flexible depending on, for example, the procedure to be performed and the size of the incision. The suspension member 40 can be formed of a resiliently deformable material, such as natural rubber, silicone, or a suitable deformable elastomer or elastomeric material. In some embodiments, more than one material can be used to form the suspension member 40, and the suspension member 40 can include some portions that are more rigid than others. For non-limiting example, the sleeve 44 can be formed from a highly flexible and resilient material such that the distal portion of the suspension member 40 can stretch and angularly diverge relative to the longitudinal axis of the working channel 28. The sleeve 44 can also be formed of a relatively low friction, puncture resistant material that allows for relatively high elongation before tearing. The sleeve 44 can also be relatively resistant to degradation by silicon or other lubricants. The rim 42 can be formed of the same material as the sleeve 44 or can be formed of a different material. Forming the rim 42 from a relatively stiff material, such as polyethylene, polycarbonate, polyester, polyetherimide material, or stainless steel, can help prevent the suspension member 40 from passing through the working channel 28.

Figure 6:
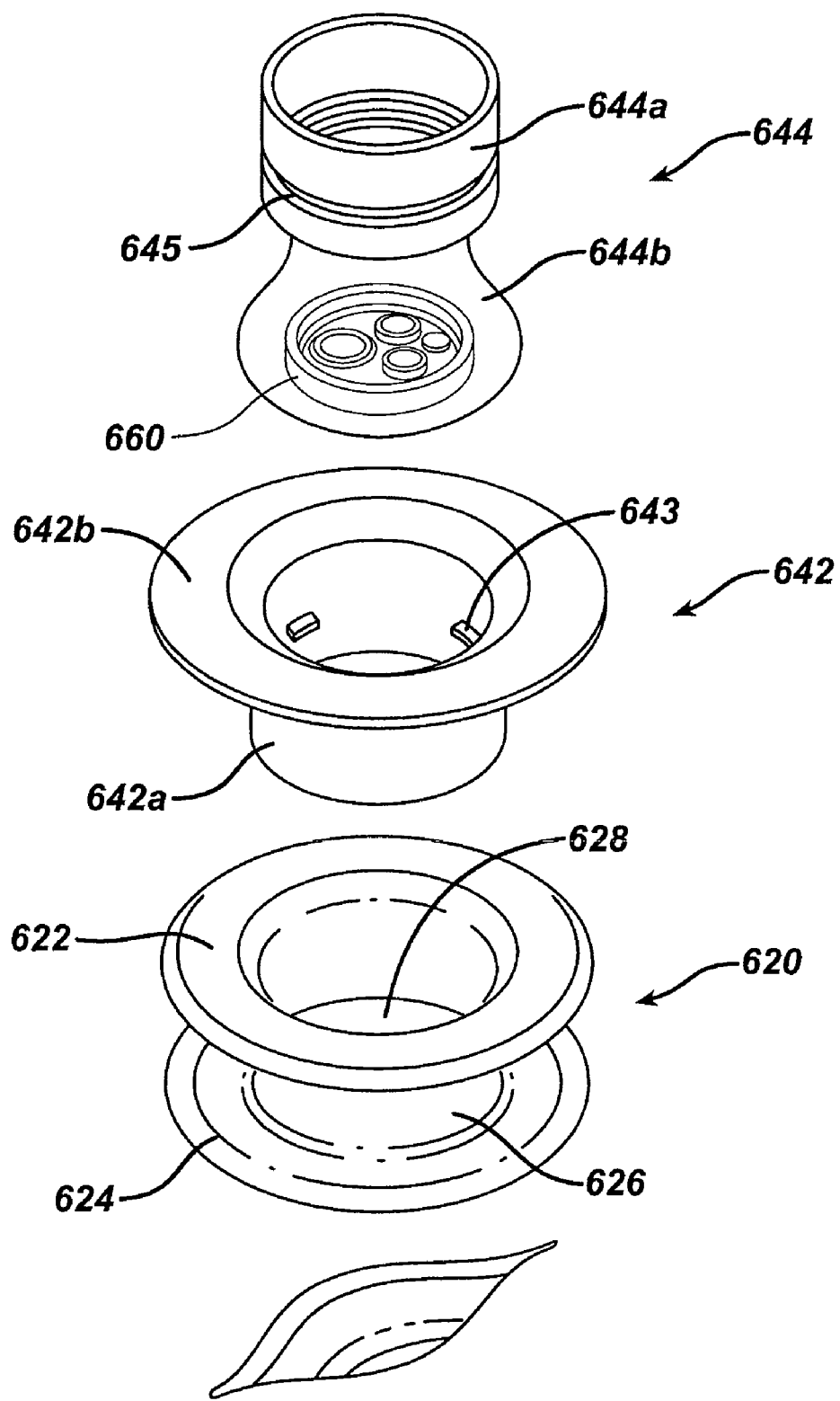
FIG. 6 is an exploded perspective view of another exemplary embodiment of a surgical access device.

The distal portion of the suspension member 40 can be integral with the proximal portion of the suspension member 40, as shown in FIGS. 1-3. The distal portion of the suspension member 40 can also be fixedly or movably coupled to the proximal portion of the suspension member 40 using any number of engagement mechanisms (e.g., snap-fit couplings, threading, etc.) known in the art. For non-limiting example, in another embodiment depicted in FIG. 6, a surgical access device 600 includes a retractor 620, seal housing 660, and suspension member having a proximal portion 642 and a distal portion 644. The proximal portion 642 includes a first tubular housing 642a having an annular rim 642b that extends radially-outward from its proximal end. The first tubular housing 642a can be of any size or shape but as shown in FIG. 6 can have an outer diameter that is approximately equal to or slightly less than the inner diameter of the working channel 628 of the retractor 620 and a shape that corresponds to the shape of the working channel of the retractor 620. The first tubular housing 642a can include an annular flange 643 formed on its inner surface. The distal portion 644 of the suspension member or tether can include a second tubular housing 644a and a flexible sheath 644b that extends distally from the distal end of the second tubular housing 644a. The distal end of the flexible sheath 644b can be configured to couple to seal housing 660. The second tubular housing 644a can have an outer diameter approximately equal to or slightly less than the inner diameter of the first tubular housing 642a. The second tubular housing 644a can include an annular groove 645 formed on its outer surface. The annular flange 643 can be configured to snap-fit into the annular groove 645 when the second tubular housing 644a is inserted into the first tubular housing 642a such that the proximal portion 642 of the suspension member couples to the distal portion 644 of the suspension member.

The distal portion of the suspension member can also include various engagement features for retaining the seal housing therein. One skilled in the art will appreciate that any number of engagement mechanisms can be used to couple the seal housing to the suspension member. In one embodiment, as shown in FIGS. 2 and 3, an annular rim 48 formed on an inner surface of the distal end of the cylindrical sleeve 44 prevents the seal housing 60 from being pressed distally beyond the distal end of the suspension member 40. The annular rim 48 can have an inner diameter $D_R$ less than a maximum outer diameter $D_S$ of the seal housing 60 such that the seal housing 60 can rest upon the annular rim 48, as shown in FIG. 3. The annular rim 48 need not be closed or continuous, but can be, for non-limiting example, a plurality of circumferentially-spaced, radially-inward extending tabs. Although the seal housing 60 rests upon the annular rim 48 in this illustrated embodiment, the suspension member 40 can couple to or mate with the seal housing 60 in any manner known in the art, e.g., annular grooves formed in an external surface of the seal housing can snap-fit with corresponding flanges formed on an inner surface of the distal portion of the suspension member 40, or flanges formed on an external surface of the seal housing 60 can snap-fit with corresponding grooves formed on an inner surface of the distal portion of the suspension member 40. The seal housing can also, for non-limiting example, slidingly or threadingly engage the suspension member or can couple by way of an interference fit. Any other engagement mechanism known in the art, e.g., adhesives, can be utilized to fixedly retain or releasably couple the seal housing 60 to the suspension member 40. Further, the seal housing 60 can engage any portion of the suspension member 40 such that the seal housing 60 can extend into the body cavity when the access device 100 is positioned within a tissue opening.

One skilled in the art will also appreciate that the engagement mechanism can be formed in or extend from any portion of the suspension member 40 or the retractor 460 such that the suspension member 40 can couple to the proximal or distal end of the seal housing 460 or any location therebetween. For non-limiting example, in another embodiment depicted in FIGS. 4-5, the suspension member of surgical access device 400 includes an annular ring 448 that is configured to mate with or couple to an annular shoulder 468 formed in the seal housing 460. Although the annular ring 448 of the suspension member is shown engaging the suspension member at a midportion of the outer surface of the seal housing 460, one skilled in the art will appreciate that the suspension member can couple to any portion of the seal housing 460 including, for example, the proximal end of the seal housing 460.

One skilled in the art will appreciate that the suspension member or tether can include additional features to help suspend a seal housing within a body cavity and provide access to an internal body cavity. For non-limiting example, the interface between the suspension member and the retractor and the suspension member and the seal housing can be configured to form an air-tight seal such that insufflation of the body cavity can be maintained. The suspension member can also include anti-inversion features to prevent the sleeve 44 from being inverted when surgical instruments disposed through the seal elements 62a, 62b, and 62c are pulled proximally. For non-limiting example, the sleeve 44 can include one or more longitudinal ribs that prevent the suspension member from turning inside-out during withdrawal of an instrument from the seal elements.

Any and all of the surgical access devices described herein can also include various other features, such as one or more ventilation ports to allow evacuation of smoke during procedures that utilize cautery, and/or one or more insufflation ports through which the surgeon can insufflate the abdomen to cause pneumoperitenium, as described by way of non-limiting example in U.S. Patent Application No. 2006/0247673 entitled "Multi-port Laparoscopic Access Device" filed Nov. 2, 2006, which is hereby incorporated by reference in its entirety. The insufflation port can be located anywhere on the device, can have any size, and can accept a leur lock or a needle, as will be appreciated by those skilled in the art. As will be appreciated by those skilled in the art, any and all of the retractor, suspension member, seal housing, and seal element embodiments disclosed herein can be configured to maintain insufflation, e.g., can be formed of a material impermeable to gases. Additionally, any couplings between any components can be configured to prevent leakage of insufflation gas from a body cavity.

In order to maintain insufflation within the body cavity, a surgical access device can include at least one seal disposed therein to prevent air and/or gas from escaping therefrom. Various sealing elements are known in the art, but typically the surgical access device can include at least one instrument seal that forms a seal around an instrument disposed therethrough, but otherwise does not form a seal when no instrument is disposed therethrough; at least one channel seal or zero-closure seal that seals the working channel created by the seal element when no instrument is disposed therethrough to thus prevent the leakage of insufflation gases delivered through the surgical access device to the body cavity; or a combination instrument seal and channel seal that is effective to both form a seal around an instrument disposed therethrough and to form a seal in the working channel when no instrument is disposed therethrough. A person skilled in the art will appreciate that various seals known in the art can be used including, e.g., duckbill seals, cone seals, flapper valves, gel seals, diaphragm seals, lip seals, iris seals, etc. A person skilled in the art will also appreciate that any combination of seals can be included in any of the embodiments described herein, whether or not the seal combinations are specifically discussed in the corresponding description of a particular embodiment. Exemplary instrument seal configurations are described in more detail in U.S. Patent Publication No. 2004/0230161 entitled "Trocar Seal Assembly," filed on Mar. 31, 2004, and U.S. patent application Ser. No. 10/687,502 entitled "Conical Trocar Seal," filed on Oct. 15, 2003, which are hereby incorporated by reference in their entireties.

The surgical access device 100 can include the seal housing 60 that can contain one or more seal elements 62a, 62b, and 62c that can maintain a seal between a surgical site and an outside environment. The seal housing 60 can generally have a proximal and distal end and can be configured to couple to the suspension member 40 such that the proximal end and/or the distal end can extend distally into the body cavity. A person skilled in the art will appreciate that the illustrated seal housing 60 is one embodiment, and that the seal housing can have a variety of configurations, shapes, and sizes. Various other exemplary seal housings are described in more detail in U.S. patent application Ser. No. 12/399,482 entitled "Methods And Devices For Providing Access Into A Body Cavity" filed Mar. 6, 2009, U.S. patent application Ser. No. 12/399,547 entitled "Surgical Access Devices And Methods Providing Seal Movement In Predefined Paths" filed Mar. 6, 2009, and U.S. patent application Ser. No. 12/399,625 entitled "Methods And Devices For Providing Access Into A Body Cavity" filed Mar. 6, 2009, which are hereby incorporated by reference in their entireties. In the embodiment depicted in FIGS. 1-3, the seal housing 60 is generally cylindrical body having a cylindrical outer surface and a proximal end with one or more openings and a distal end with one or more openings. One or more bores or ports can extend through or be formed in the cylindrical body and align with the one or more openings of the proximal and distal ends such that each bore or port can be configured to contain a seal element 62a, 62b, and 62c. The bores or ports can have any shape, size, and configuration that allow a seal element 62a, 62b, and 62c to be disposed therein and a surgical instrument to pass therethrough.

The shape, size, number, and purpose of the seal elements 62a, 62b, and 62c can vary. As depicted in FIGS. 1-3, the seal housing 60 contains three seal elements 62a, 62b, and 62c. As discussed above, the seal elements 62a, 62b, and 62c can each include at least one instrument seal and/or at least one channel seal, and can generally be configured to contact an instrument inserted through the seal element. While each of the seal elements 62a, 62b, and 62c can have a different size and/or shape, the illustrated embodiment depicts two seal elements 62b, 62c of approximately equal size and one seal element 62a that is relatively larger. Seal elements of different sizes and shapes can be mixed and matched to allow a surgeon to configure a desired set-up for use with a particular surgical procedure on a particular patient. The seal elements used in the surgical access device can also be removable, replaceable, and interchangeable. The seal elements can be fixed relative to the seal housing or can be rotatable or movable.

The seal elements 62a, 62b, and 62c can be made of a variety of materials, but can generally be configured to be flexible such that surgical instruments can be moveable within the seal element without breaking the seal. Examples of flexible materials that can be used to form the seal elements 62a, 62b, and 62c include polyisoprene, polyurethane, and silicone. In some embodiments, the seal elements 62a, 62b, and 62c can be made of rigid or semi-rigid materials to help protect any instruments disposed therethrough and to maintain the general location of the seal elements 62a, 62b, and 62c within the seal housing 60.

FIGS. 7A-7D illustrate one embodiment of a seal housing insert assembly 2000 that can be used with the present invention. The insert assembly 2000 can include an outer body portion 2100, a bearing member 2200, an inversion constraint member 2300, a spacer 2400, an elastomeric instrument channel member 2500, a membrane seal 2600, and an inner housing 2700, as described more fully below.

Outer body portion 2100 is shown in the form of a generally cylindrical shell having a generally cylindrical outer surface 2110, an inner surface 2112, a distal ledge 2120 extending radially inwardly from surface 2112, and an internal surface feature, such as circumferentially extending protrusions 2114. The outer body portion 2100 can be a generally rigid, hard shell formed of a suitable material, such as polyethylene or other suitable medical grade materials, so that when the insert 2000 is inserted into a flexible retractor, the outer body portion 2100 does not deform to any significant degree, but instead can act to radially or circumferentially stretch or otherwise expand the working channel of a flexible retractor to a desired shape and size. The outer body portion 2100 can also be sized and shaped to pass through the working channel and remain retained within the suspension member. For instance, the outer body portion 2100 can have a generally cylindrical outer surface 2110 having an outer diameter smaller than the diameter of the working channel and larger than the diameter of an annular rim formed on an inner portion of a suspension member or tether. Although the insert 2000 and outer body portion 2100 are shown having a generally circular cross-sectional shape, the insert 2000 and outer body portion 2100 can have any shape, for example and without limitation, circular, ovular, rectangular, and triangular. A circular cross-sectional shape can ease rotation of the insert 2000 with respect to a suspension member in which it is retained.

The inner housing 2700 of the insert 2000 can include an outer proximally facing top surface 2702 through which one or more instrument openings 2014 can extend. The inner housing 2700 can also have a generally cylindrical outer side surface 2710 extending distally from the top surface 2702. The protrusions 2114 formed in the inner surface of outer body portion 2100 can operatively engage a feature of the inner housing 2700, such as a circumferentially extending groove 2714 formed the outer surface 2710 of the inner housing 2700. The protrusions 2114 can engage the groove 2714 to restrain the inner housing 2700 axially (i.e. in the proximal and distal directions) with respect to the outer body portion 2100, while permitting rotation of the inner housing 2700 with respect to the outer body portion 2100. Alternatively, the body portion 2100 can include a groove, and the inner housing 2700 can include a protrusion for engaging such a groove.

Figure 7A:
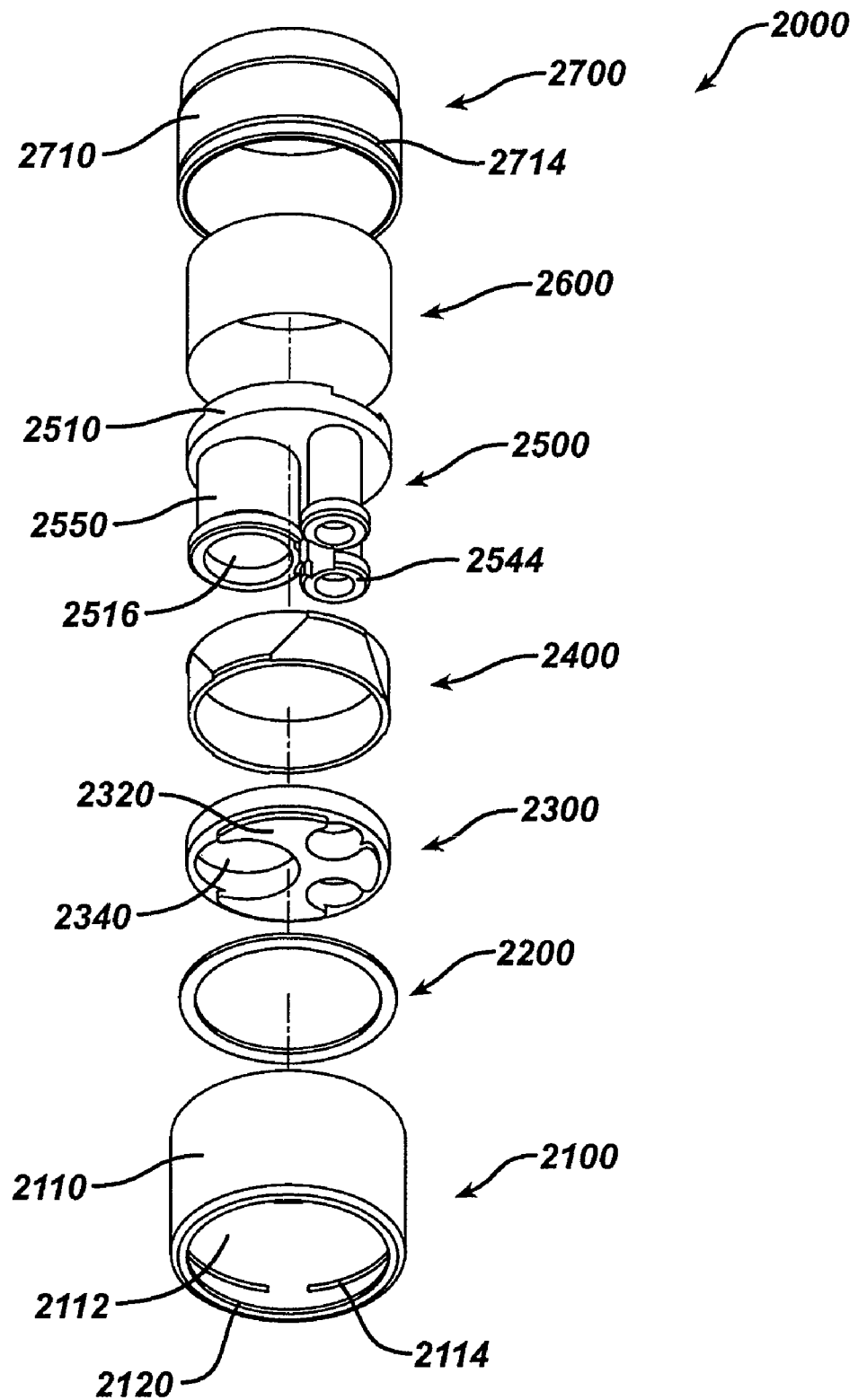
FIG. 7A is an exploded view of one embodiment of a seal housing.
Figure 7B:
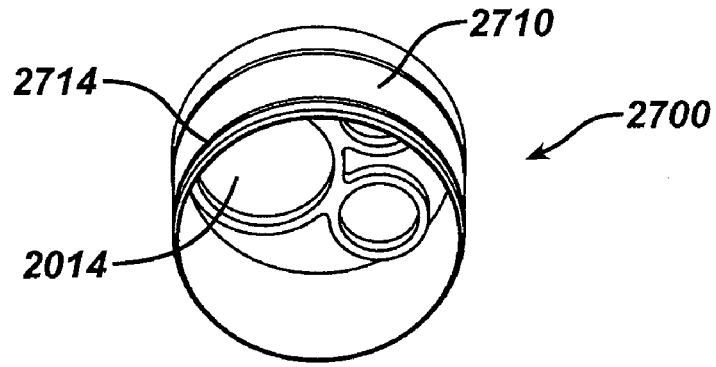
FIG. 7B is a bottom perspective view of the inner housing of the device of FIG. 7A.
Figure 7C:
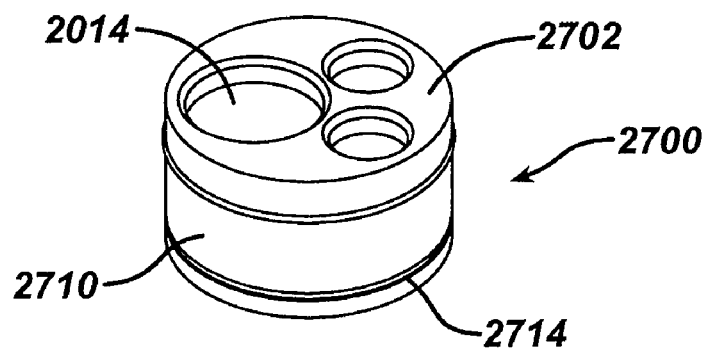
FIG. 7C is a top perspective view of the inner housing of the device of FIG. 7A.
Figure 7D:
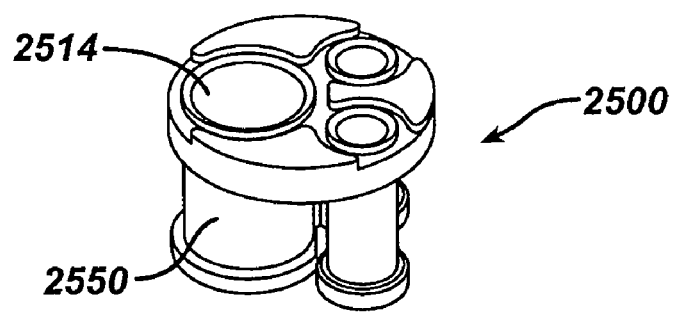
FIG. 7D is a top perspective view of the instrument channel member of the device of FIG. 7A.

An instrument channel member 2500 can be supported within the inner housing 2700. The instrument channel member 2500 can include base 2510 and one or more instrument channels 2550, with each channel 2550 generally aligned with and extending from a proximal opening 2514 in the base to a distal exit 2516. The instrument channel member 2500 can be formed as a unitary structure formed from a deformable, resilient material such as polyisoprene, Kraton, or Sanoprene, so that each instrument channel 2550 is independently deformable with respect to the housing 2700 and to the other instrument channels. Accordingly, surgical instruments inserted into the instrument channels 2550 can be angled and/or pivoted with respect to each other, allowing for increased freedom of motion of each instrument relative to the others. A seal or other constriction can be provided within each instrument channel 2550 for providing sealing about an instrument positioned within the instrument channel 2550. As shown in FIG. 7A, a seal element 2544 can be provided at the distal end of each instrument channel 2550. As will be discussed below, any seal known in the art can form the seal element 2544.

A membrane seal 2600 can be captured between the inner housing 2700 and the instrument channel member 2500. The membrane seal 2600 can be a generally cylindrical member that can include a thin membrane extending across its upper surface. The thin membrane can be formed of a flexible material which can be punctured or otherwise pierced by a surgical instrument to can prevent loss of insufflation through an instrument opening 2014 prior to insertion of an instrument through the opening. In one embodiment, the membrane seal 2600 can include, for non-limiting example, a membrane formed of polyurethane having a thickness of less than about 0.010 inch, and in particular a thickness of about 0.006 inch. Alternatively, a zero closure seal such as a duckbill seal or other suitable seal for sealing in the absence of instrument can be employed in association with the instrument channels 2550.

The distal ledge 2120 of the outer body portion 2100 can provide an axial thrust support surface on which a bearing member 2200 can be rotatably supported. The bearing member 2200 can be an annular member and can provide rotational support for the inner housing 2700 and the instrument channel member 2500, such that the inner housing 2700 and channel member 2500 can rotate relative to the outer body portion 2100 about a longitudinal axis of the working channel of a retractor when the insert 2000 is retained by a suspension member or tether. The bearing member 2200 can be formed of any suitable material, such as high density polyethylene. Rotation of the channel member 2500 can permit rotational positioning of the instrument openings 2014 and channels 2550 to provide desired positioning of one or more instruments extending through insert 2000.

Inversion constraint member 2300 can be provided to prevent the instrument channels 2550 from becoming "inverted" (e.g. in the manner of a shirt sleeve being pulled inside out) when an instrument is withdrawn from the channel 2550. The inversion constraint member 2300 can have a generally disc shaped body 2320 having one or more apertures 2340 extending therethrough. Each aperture 2340 can be sized to fit over the distal end of a corresponding instrument channel 2550. The inversion constraint member 2300 can be formed of any suitable material, including for instance polyisoprene, Sanoprene, or Kraton. The flexibility of the member 2300 can be tailored with respect to the flexibility of more proximal portions of the insert 2000. For instance, if inversion constraint member 2300 is made relatively more flexible than a proximal portion of the insert 2000 (such as for instance the top surface of the housing 2700), then instruments inserted in the instrument channels will tend to pivot about a fulcrum associated with the more proximal portion of the insert. Alternatively, if the inversion constraint member 2300 is made relatively more rigid with respect to the more proximal portions of the insert 2000, then the instruments will tend to pivot about a fulcrum associated with the member 2300. The inversion constraint member 2300 can be positioned axially between the bearing member 2200 and spacer 2400, and the inversion constraint member 2300 can be positioned radially inward of the distal portion of the inner housing 2700. The spacer 2400 can maintain the channels 2550 at a preferred height and can consist of a generally cylindrical member that can extend between the inversion constraint member and the base 2510 of the instrument channel member 2500.

One skilled in the art will appreciate that the seal housing can have a variety of configurations, shapes, and sizes. Other exemplary seal housing configurations are described in more detail in U.S. application Ser. No. 12/399,473 entitled "Methods and Devices for Providing Access into a Body Cavity," filed on Mar. 6, 2009, and U.S. application Ser. No. 12/399,547 entitled "Surgical Access Devices and Methods Providing Seal Movement in Predefined Paths," filed on Mar. 6, 2009, and U.S. application Ser. No. 12/399,625 entitled "Methods and Devices for Providing Access into a Body Cavity," filed on Mar. 6, 2009, which are hereby incorporated by reference in their entireties.

Referring back to FIGS. 1-3, in use the surgical access device 100 can be inserted into an incision or opening in the body wall to provide surgical access to an internal body cavity. In particular, after an incision is made, the retractor 20 can be inserted through the incision and positioned such that the distal flange 22 extends into the patient's body cavity and engages an inner surface of the body wall. In one embodiment, at least a portion of the retractor 20 can be sufficiently flexible such that the retractor 20 can be easily maneuvered through the incision. Upon insertion, the retractor 20 can return to its original configuration such that the retractor 20 provides the working channel 28 through which surgical instruments can be inserted into the body cavity. The suspension member 40 can then be inserted into the retractor 20, e.g., by pressing the sleeve 44 into the working channel 28 until the rim 42 abuts the proximal flange 22 of the retractor 20. The proximal end of the seal housing 60 can extend distally beyond the distal end of the retractor 20 such that the seal housing is not radially restrained by the working channel 28. The seal housing 60 can be pre-loaded in the suspension member 40 or it can be inserted into the passageway 46 after the retractor 20 is implanted and such that the seal housing 60 rests on the rim 48 and is suspended within the body cavity. Surgical instruments can then be passed through the passageway 46 and inserted through a seal element 62a, 62b, and 62c of the seal housing 60. The surgical instruments can then be manipulated as required by the surgical procedure. As the instruments are obliquely oriented relative to the working channel 28, the sleeve 44 can flex, e.g., stretch, bend, deform, contort, or otherwise move, to allow the seal housing 60 to be obliquely oriented relative to the retractor 20. The seal housing 60 can also move axially along the longitudinal axis of the working channel and can move radially relative to the longitudinal axis of the working channel. In other words, the seal housing 60 will move with the surgical instrument and out of alignment with the longitudinal axis of the working channel 28 so that a seal is maintained around the instrument. If a specimen needs to be removed, or other access is needed, the surgical instruments can be removed from the seal elements 62a, 62b, and 62c and the suspension member 40 can be removed from retractor 20. The specimen can then be removed through the working channel 28 of the retractor 20. One skilled in the art will appreciate that the surgical access device 100 can be assembled in any order. For non-limiting example, the seal housing 60 can be coupled to the suspension member 40 before or after the suspension member is coupled to the retractor 20.

Figure 8:
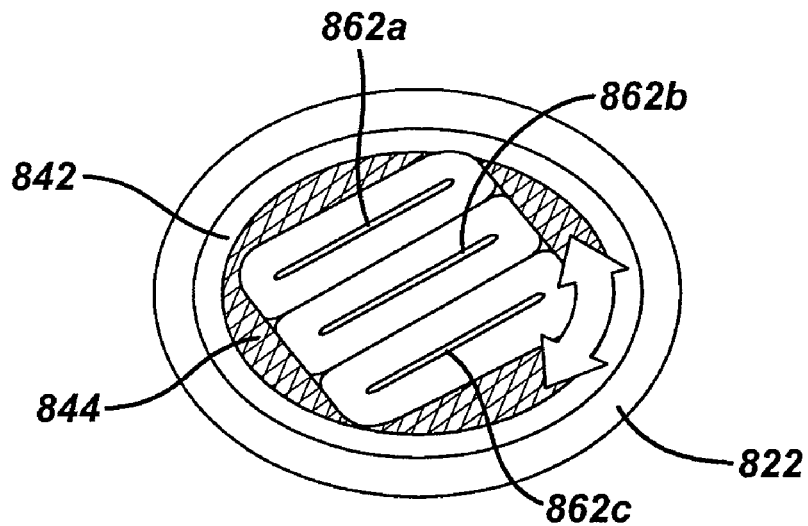
FIG. 8 is a top view of another exemplary embodiment of a surgical access device.
Figure 9:
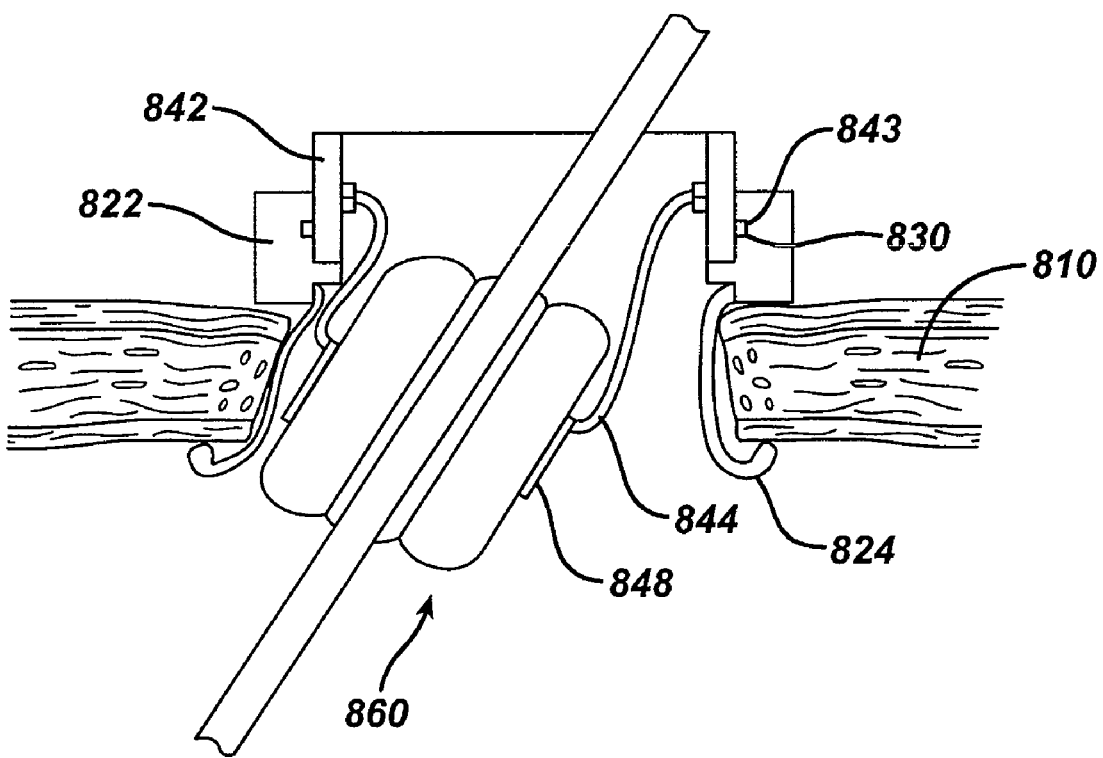
FIG. 9 is a side cross-sectional view of the device of FIG. 7 disposed in an opening formed in tissue.

Another exemplary embodiment of a surgical access device of the present invention is shown in FIGS. 8-9. Like the surgical access device 100 of FIGS. 1-3, the surgical access device 800 can include a retractor for providing a working channel through tissue, a suspension member or tether having a proximal portion 842 and a distal portion 844, and a seal housing 860 having at least one seal element 862a, 862b, and 862c disposed therein.

The retractor of the embodiment depicted in FIGS. 8-9 can have proximal and distal ends and a working channel extending therethrough. The proximal and distal ends can have any suitable configuration that allow the retractor to be secured within the incision. As shown in FIGS. 8-9, the proximal end of the retractor can include a retractor housing 822 that can be disposed outside the patient's body and that can engage an outer surface of the patient's body wall 810 when positioned during surgery. The retractor housing 822 can form the proximal end of retractor or can be a separate component that is fixedly or removably coupled to the proximal end of the retractor using any method known in the art. The retractor housing 822 can be generally annular and can have any shape such as a closed or substantially closed configuration having, for non-limiting example, a circular, oval, elliptical, square, or rectangular shape. The retractor housing 822 can additionally include engagement features for coupling to the proximal end of the suspension member. One skilled in the art will appreciate that any known engagement mechanisms can be used to couple the suspension member to the retractor housing 822.

The distal end of the retractor of FIGS. 8-9 can also have any suitable configuration that allows the retractor to be secured within the incision. For example, the distal end of the retractor can be formed as an annular flange as discussed above in reference to FIGS. 1-3. Alternatively, the retractor can include a flexible skirt 824 that can help maintain the working channel in an open configuration. The skirt 824 can flare radially outward as the retractor extends distally through the body wall 810 when the retractor is placed in an incision. The external surfaces of the skirt 824 can include surface features to help securely engage the retractor 824 to the patient's body wall 810.

The retractor of the embodiment depicted in FIGS. 8-9 can be rigid, semi-rigid, or flexible and can be formed of any suitable material. In some embodiments, more than one material can be used to form the retractor housing 822 and the skirt 824, and the retractor can include some portions that are more rigid than others. For non-limiting example, the skirt 824 can be formed of a resiliently deformable material, such as natural rubber, silicone, or a suitable deformable elastomer or elastomeric material while the retractor housing 822 can be formed of a stiffer material, such as polyethylene, polycarbonate, polyester, polyetherimide material, or stainless steel. For example, the skirt 824 can be deformed to ease insertion through an incision in the body wall 810. Once the skirt 824 is fully inserted through the incision, the skirt 824 can be released and can resiliently return to its undeformed configuration to maintain open the working channel 828.

The suspension member or tether of the embodiment depicted in FIGS. 8-9 can have a variety of configurations, but in one exemplary embodiment, the proximal portion of the suspension member can include a collar 842 that is configured to couple to the retractor housing 822. The collar 842 can define a passageway through which instruments can be passed into the working channel 828. The collar 842 can have any shape but generally has the same shape as the retractor housing 822 to which it couples. One skilled in the art will appreciate that any number of engagement mechanisms can be used to fixedly or removably couple the collar 842 to the retractor housing 822. As shown in the embodiment depicted in FIG. 9, an annular flange 843 can extend from an external surface of the collar 842 for snap-fitting into a corresponding annular groove 830 formed on an internal surface of the retractor housing 822 when the collar 842 is inserted into the retractor housing 822. The collar 842 can also slidingly or threadingly engage the retractor housing 822 or can couple in any other way, e.g., by way of an interference fit. The collar 842 can also be coupled to the retractor housing 822 such that the collar 842 can be rotated relative to the retractor housing 822. The collar 842 can be rigid, semi-rigid, or flexible and can be formed of any suitable material. In some embodiments, more than one material can be used to form the collar 842, and the collar 842 can include some portions that are more rigid than others.

One skilled in the art will appreciate that any number of coupling mechanisms can be used to fixedly or removably couple a sleeve 844 to the collar 842. For example, the sleeve 844 can be coupled by snap-fit or interference fit or with an adhesive to the collar 842. The sleeve 844 can also be integral with the collar 842. The sleeve 844 can be formed of any highly flexible and resiliently deformable material, such as natural rubber, silicone, or a suitable deformable elastomer or elastomeric material such that the sleeve 844 can stretch and angularly diverge relative to a longitudinal axis of the working channel. The sleeve 844 can also be formed of a relatively low friction, puncture resistant material that allows for relatively high elongation before tearing. The sleeve 844 can also be formed of a material that is relatively resistant to degradation by silicon or other lubricants. The sleeve 844 can have any length but preferably has a fully-extended length greater than or equal to the height of the retractor such that the seal housing 860 coupled to the distal end of the sleeve 844 can distally extend into the body cavity beyond the distal end of the retractor when the retractor is positioned in tissue. Further, the sleeve 844 can be configured to extend distally beyond the distal end of the retractor a sufficient distance such that the proximal end of the seal housing 860 is disposed distally beyond the distal end of the retractor. The sleeve 844 can additionally include anti-inversion features to prevent the sleeve 844 from being inverted or pulled proximally through the proximal end of the working channel.

The sleeve 844 can be coupled to the seal housing 860 and can suspend the seal housing 860 at a first position within the working channel. One skilled in the art will appreciate that any number of coupling mechanisms can be used to fixedly or removably couple the sleeve 844 to the seal housing 860. Alternatively, the sleeve 844 can be integral with the seal housing 860 such that the seal housing 860 and the sleeve 844 are formed as a single component. In one exemplary embodiment, as shown in FIG. 9, the distal end of the sleeve 844 can include an elastomeric molded sleeve 848. The molded sleeve 848 can be configured to surround at least a portion of the external surface of the seal housing 860. The molded sleeve 848 can have a resting diameter less than a diameter of the seal housing 860 such that the molded sleeve 848 can be stretched to surround the seal housing 860. The resilient elastomeric molded sleeve 848 can compress against an outer surface of the seal housing 860 to form an air-tight seal. Any other engagement mechanism known in the art can also be utilized to fixedly retain or releasably couple the seal housing 860 to the sleeve 844. Further, any portion of the suspension member can engage any portion of the seal housing 860 such that the seal housing 860 is capable of extending into the body cavity.

One skilled in the art will appreciate that the seal housing 860 can have a variety of configurations, shapes, and sizes. As depicted in FIGS. 8-9, the seal housing 860 can contain three seal elements 862a, 862b, and 862c. While each of the seal elements 862a, 862b, and 862c can have a different size and/or shape than the other seal elements, the illustrated embodiment depicts three parallel slit seals formed in the seal housing 860. The seal housing 860 can be formed of a resilient and compressible material such that the walls of the slit seal elements 862a, 862b, and 862c can conform to a surgical instrument inserted therethrough to maintain the seal between the body cavity and the outside environment. When the instrument is removed, the resilient material of the seal housing 860 can reseal itself.

In use, the surgical access device 800 of FIGS. 8-9 can be similarly inserted within an incision as discussed above in reference to the surgical access device 100 of FIGS. 1-3. The seal housing 860 can be coupled to the distal end of the sleeve 844 and can be suspended at a first position within the working channel 828 of the retractor. Surgical instruments can then be passed through the seal elements 862a, 862b, and 862c disposed in the seal housing 860 and can be manipulated such that the sleeve 844 extends distally through working channel 828. The sleeve 844 can flex, e.g., stretch, bend, deform, contort, or otherwise move to allow the seal housing 860 to be distally extended beyond the distal end of the retractor and/or to be angularly oriented relative to the retractor. For non-limiting example, sleeve 844 can flex similar to the movement of sleeve 444 of surgical access device 400 depicted in FIGS. 4 and 5.

Figure 10:
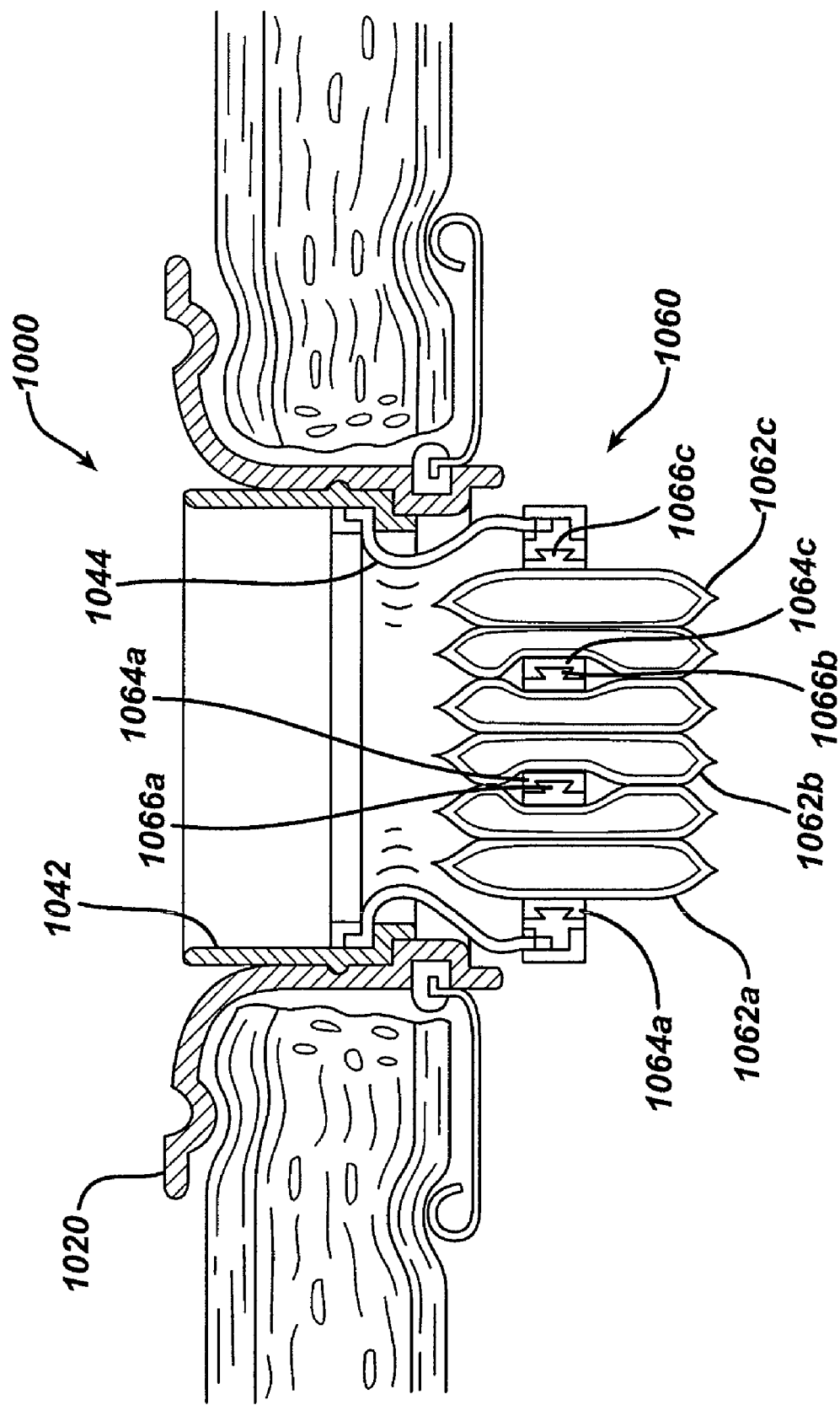
FIG. 10 is a side cross-sectional view of another exemplary embodiment of a surgical access device.

Another exemplary embodiment of a surgical access device 1000 is shown in FIG. 10. The surgical access device 1000 is similar to the surgical access device 400 of FIG. 4 and can include a seal housing 1060 having one or more interchangeable seal elements 1062a, 1062b, and 1062c. The surgical access device 1000 can include a suspension member or tether that suspends seal housing 1060 from the retractor 1020. A tubular housing 1042 can be configured to be disposed within the working channel of the retractor 1020. The external surface of the tubular housing 1042 can include an engagement mechanism to engage the retractor 1020. The tubular housing 1042 can be coupled to a flexible sleeve 1044 which in turn can be coupled to the seal housing 1060. Each of the seal elements 1062a, 1062b, and 1062c can include a mating element that allows the seal elements 1062a, 1062b, and 1062c to couple to each other to form a seal between a surgical site within a body cavity and an outside environment. For example, each of the seal elements 1062a, 1062b, and 1062c can include a single rail 1064a, 1064b, and 1064c and a single guide 1066a, 1066b, and 1066c, respectively, that can be complimentary to adjacent guides and rails of the other seal elements 1062a, 1062b, and 1062c and an engagement mechanism 1048 for coupling to the sleeve 1044. The seal elements 1062a, 1062b, and 1062c can be formed of a flexible material such that the seal elements 1062a, 1062b, and 1062c can conform around a surgical instrument when an instrument is inserted therethrough. The seal elements 1062a, 1062b, and 1062c can be integral with or can be coupled to the rails 1064a, 1064b, and 1064c and guides 1066a, 1066b, and 1066c. The rails 1064a, 1064b, and 1064c and guides 1066a, 1066b, and 1066c can be formed of the same material as the sealing elements 1062a, 1062b, and 1062c, or can be formed of a stiffer material, such as polyethylene or stainless steel. Accordingly, surgical access device 1000 can allow a surgeon to adapt the seal housing 1060 and interchange the seal elements 1062a, 1062b, and 1062c. Further discussion of interchangeable seal elements that can be used in conjunction with the disclosed systems, devices, and methods, are described in greater detail in U.S. application Ser. No. 12/479,096 entitled "Interlocking Seal Components" of Shelton et al. filed on Jun. 5, 2009, which is hereby incorporated by reference in its entirety.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

Further, any and all of the various embodiments of the retractor, suspension member or tether, seal housing, and seal element embodiments disclosed herein can be interchangeable with one another as needed. For example, a kit can include multiple retractors, suspension members or tethers, and seal housings having a variety of seal elements. A surgeon can select the appropriate size, shape, and configuration of each component.

As surgical instruments are inserted through the surgical access device embodiments described herein, a risk can exist that a particularly sharp instrument can tear or puncture a portion of the retractor, suspension member or tether, seal housing, seal element or nearby tissue. Accordingly, in any and all of the embodiments described herein, a safety shield can optionally be included to reduce the risk of tearing or puncture by a surgical instrument. In general the shield can be of a material that is relatively smooth to allow ease of passage of instruments, but resistant to tearing and puncture. For example, the shield can be formed of silicone, urethane, thermoplastic elastomer, rubber, polyolefins, polyesters, nylons, fluoropolymers, and any other suitable materials known in the art. The shield can generally provide a liner for the retractor or tissue and can be detachable from a surgical access device so it can be used as needed in a particular procedure. The shield can also be integral with the any of the surgical access device embodiments or any of the components described herein. The components themselves can also act as shields.

In any and all of the surgical access device embodiments disclosed herein, an engagement and/or release mechanism can be included to allow one component to be separated from another component or to allow one portion of a component to be separated from another portion of a component. For example, a seal element can be separable from the seal housing. The engagement or release mechanism can be a latch, switch, c-clamp, tabs, push button, or any other mechanism known in the art that can be configured to release one portion of a device from another.

There are various features that can optionally be included with any and all of the surgical access device embodiments disclosed herein. For example, a component of the device, such as the retractor, suspension member or tether, or seal housing, can have one or more lights formed thereon or around a circumference thereof to enable better visualization when inserted within a patient. As will be appreciated, any wavelength of light can be used for various applications, whether visible or invisible. Any number of working channels, suspension members or tethers, seal housings, and seal elements can be included on and/or through the retractor to enable the use of various surgical techniques and devices as needed in a particular procedure. For example, openings and ports can allow for the introduction of pressurized gases, vacuum systems, energy sources such as radiofrequency and ultrasound, irrigation, imaging, etc. As will be appreciated by those skilled in the art, any of these techniques and devices can be removably attachable to the surgical access device and can be exchanged and manipulated as needed.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, new or used surgical instruments and access devices are obtained and cleaned, if necessary. The surgical equipment can then be sterilized. Any number of sterilization techniques known to those skilled in the art can be used to sterilize the equipment including beta or gamma radiation, ethylene oxide, steam, and a liquid bath (e.g., cold soak). In one sterilization technique, the equipment is placed in a closed and sealed container, such as a plastic or TYVEK bag. The container and equipment are then placed in a field of radiation that can penetrate the container, such as gamma radiation, x-rays, or high-energy electrons. The radiation kills bacteria on the equipment and in the container. The sterilized equipment can then be stored in the sterile container. The sealed container keeps the equipment sterile until it is opened in the medical facility.

What is claimed is:

1. A surgical access device, comprising:
a flexible retractor having a working channel extending therethrough; and
a seal housing defining a plurality of ports, each port having a sealing elements disposed therein and configured to form a seal around an instrument inserted therethrough, the seal housing being freely movably suspended within a distal portion of the flexible retractor by a flexible tether coupled to the flexible retractor such that at least a portion of the seal housing can extend distally beyond the distal end of the retractor and can be freely angularly oriented relative to the retractor.

2. The device of claim 1, wherein the flexible tether includes a proximal housing that is rotatably coupled to a retractor housing on the flexible retractor.

3. The device of claim 1, wherein the flexible tether includes a cylindrical distal portion and a proximal flange that rests against a proximal end of the retractor.

4. The device of claim 1, wherein the seal housing is configured to form a seal across the working channel of the retractor.

5. The device of claim 1, wherein the distal portion of the flexible tether includes an engagement feature configured to removably engage the seal housing.

6. A surgical access device, comprising:
a retractor having proximal and distal ends with a working channel extending therethrough, the proximal end being configured to be positioned adjacent to an external surface of tissue and the distal end being configured to extend into a body cavity such that the working channel provides a pathway through the tissue;
a suspension member having a proximal portion configured to couple to the proximal end of the retractor and a distal portion that extends through the working channel of the retractor; and
a seal housing disposed within the distal portion of the suspension member and having at least one sealing element disposed therein and configured to form a seal around an instrument disposed therethrough, the seal housing having a proximal end positioned distal of the distal end of the retractor;
wherein at least a portion of the suspension member is flexible to allow the seal housing to extend beyond the distal end of the retractor.

7. The device of claim 6, wherein the distal portion of the suspension member is formed from a resilient material.

8. The device of claim 6, wherein the distal portion of the suspension member includes an engagement feature configured to removably engage the seal housing.

9. The device of claim 8, wherein the engagement feature comprises an annular member having an inner diameter less than a maximum outer diameter of the seal housing such that the annular member is configured to retain the seal housing within the distal portion of the suspension member.

10. The device of claim 6, wherein the retractor comprises a hollow flexible cylindrical member having a mid-portion with a maximum diameter that is less than a maximum diameter of the proximal and distal ends of the retractor such that the mid-portion is configured to be positioned within an opening in tissue and the proximal and distal ends are configured to engage the tissue therebetween.

11. The device of claim 6, wherein the distal portion of the suspension member comprises a flexible sleeve.

12. The device of claim 6, wherein the distal portion of the suspension member is substantially cylindrical, and the proximal portion of the suspension member comprises a radially-outward extending flange that is configured to rest against the proximal end of the retractor.

13. The device of claim 12, wherein a distal end of the suspension member includes an annular rim formed on an inner surface thereof and is configured to retain the seal housing within the distal portion of the suspension member.

14. The device of claim 6, wherein the proximal portion of the suspension member comprises a collar that is mated to a housing on the proximal end of the retractor, and the distal portion of the suspension member comprises a flexible sleeve.

15. The device of claim 14, wherein a distal end of the flexible sleeve is coupled to an annular member configured to engage the seal housing.

16. The device of claim 14, wherein the collar is rotatably mated to the housing on the retractor.

17. The device of claim 6, wherein the at least one sealing element comprises a plurality of sealing elements.

18. The device of claim 6, wherein the seal housing is configured to form a seal across the working channel of the retractor.

19. A method for accessing a body cavity, comprising:
positioning a flexible retractor within tissue such that a working channel of the flexible retractor forms a pathway through the tissue and into a body cavity;
inserting a surgical instrument through a sealing element in a seal housing suspended within the body cavity by a flexible tether extending between the seal housing and a proximal portion of the flexible retractor to position a distal end of the surgical instrument in the body cavity; and
removing the flexible tether and seal housing from the retractor leaving the retractor disposed within the tissue.

20. The method of claim 19, further comprising manipulating the surgical instrument to cause the seal housing to move relative to the flexible retractor, thereby causing the flexible tether to flex.

21. The method of claim 19, further comprising inserting a second surgical instrument through a second sealing element in the seal housing to position a distal end of the second surgical instrument in the body cavity.

* * * * *